United States Patent
Milz et al.

(10) Patent No.: US 11,622,867 B2
(45) Date of Patent: *Apr. 11, 2023

(54) SPINAL IMPLANTS

(71) Applicant: Stryker European Operations Holdings LLC, Kalamazoo, MI (US)

(72) Inventors: Bryan D. Milz, Florida, NY (US); Thomas A. Alheidt, Sussex, NJ (US); Jessica Cetrangol, Westwood, NJ (US); Christian Karl Schultz, Hoboken, NJ (US); Jason Steinke, Hoboken, NJ (US); Steven Willis, Mahwah, NJ (US); Robert Cipoletti, Pompton Plains, NJ (US); Charles L. Bush, Jr., Wayne, NJ (US); Brad Juchno, Yardley, PA (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 233 days.

This patent is subject to a terminal disclaimer.

(21) Appl. No.: 17/071,539

(22) Filed: Oct. 15, 2020

(65) Prior Publication Data

US 2021/0038404 A1 Feb. 11, 2021

Related U.S. Application Data

(63) Continuation of application No. 16/135,432, filed on Sep. 19, 2018, now Pat. No. 10,835,388.
(Continued)

(51) Int. Cl.
*A61F 2/44* (2006.01)

(52) U.S. Cl.
CPC .......... *A61F 2/447* (2013.01); *A61F 2/4455* (2013.01)

(58) Field of Classification Search
CPC .............. A61F 2/30749; A61F 2/30771; A61F 2/4425; A61F 2/4455; A61F 2/447;
(Continued)

(56) References Cited

U.S. PATENT DOCUMENTS

| | | | |
|---|---|---|---|
| 3,486,505 A | 12/1969 | Morrison | |
| 3,641,590 A | 2/1972 | Michele | |

(Continued)

FOREIGN PATENT DOCUMENTS

| | | |
|---|---|---|
| DE | 10052008 C1 | 8/2002 |
| DE | 202013007361 U1 | 3/2014 |

(Continued)

OTHER PUBLICATIONS

Search Report for European Application No. 21158679.7 dated Sep. 24, 2021. 3 pgs.

(Continued)

*Primary Examiner* — Eric S Gibson
(74) *Attorney, Agent, or Firm* — Lerner, David, Littenberg, Krumholz & Mentlik, LLP

(57) ABSTRACT

Disclosed herein is a spinal implant with a solid frame and a porous inner layer. The implant may have a cavity defined by the porous inner layer. The solid frame may have one or more ribs extending from a medial wall to a lateral wall. The thickness of the porous layer may vary relative the thickness of the solid frame at various locations. An inserter to place a spinal implant and a method to perform same are also disclosed.

20 Claims, 30 Drawing Sheets

Related U.S. Application Data

(60) Provisional application No. 62/560,910, filed on Sep. 20, 2017.

(58) Field of Classification Search
CPC .................. A61F 2/4601; A61F 2/4611; A61F 2002/30148; A61F 2002/30156; A61F 2002/30166; A61F 2002/30324; A61F 2002/30471; A61F 2002/30807; A61F 2002/30904; A61F 2002/3092; A61F 2002/3093; A61F 2002/443
See application file for complete search history.

(56) References Cited

U.S. PATENT DOCUMENTS

| | | |
|---|---|---|
| 3,852,045 A | 12/1974 | Wheeler et al. |
| 3,855,638 A | 12/1974 | Pilliar |
| 4,047,524 A | 9/1977 | Hall |
| 4,501,269 A | 2/1985 | Bagby |
| 4,612,160 A | 9/1986 | Donlevy et al. |
| 4,653,489 A | 3/1987 | Tronzo |
| 4,681,589 A | 7/1987 | Tronzo |
| 4,718,914 A | 1/1988 | Frey et al. |
| 4,743,262 A | 5/1988 | Tronzo |
| 4,820,305 A | 4/1989 | Harms et al. |
| 4,834,757 A | 5/1989 | Brantigan |
| 4,946,378 A | 8/1990 | Hirayama et al. |
| 5,071,437 A | 12/1991 | Steffee |
| 5,156,628 A | 10/1992 | Kranz |
| 5,180,381 A | 1/1993 | Aust et al. |
| 5,192,327 A | 3/1993 | Brantigan |
| 5,263,986 A | 11/1993 | Noiles et al. |
| 5,306,309 A | 4/1994 | Wagner et al. |
| 5,314,477 A | 5/1994 | Marnay |
| 5,370,692 A | 12/1994 | Fink et al. |
| 5,431,658 A | 7/1995 | Moskovich |
| 5,443,514 A | 8/1995 | Steffee |
| 5,443,515 A | 8/1995 | Cohen et al. |
| 5,458,643 A | 10/1995 | Oka et al. |
| 5,489,308 A | 2/1996 | Kuslich et al. |
| 5,504,300 A | 4/1996 | Devanathan et al. |
| 5,507,816 A | 4/1996 | Bullivant |
| 5,514,180 A | 5/1996 | Heggeness et al. |
| 5,609,635 A | 3/1997 | Michelson |
| 5,672,284 A | 9/1997 | Devanathan et al. |
| 5,683,394 A | 11/1997 | Rinner |
| 5,702,449 A | 12/1997 | McKay |
| 5,702,455 A | 12/1997 | Saggar |
| 5,709,683 A | 1/1998 | Bagby |
| 5,713,899 A | 2/1998 | Marnay et al. |
| 5,723,011 A | 3/1998 | Devanathan et al. |
| 5,734,959 A | 3/1998 | Krebs et al. |
| 5,768,134 A | 6/1998 | Swaelens et al. |
| 5,776,199 A | 7/1998 | Michelson |
| 5,885,299 A | 3/1999 | Winslow et al. |
| 5,893,889 A | 4/1999 | Harrington |
| 5,961,554 A | 10/1999 | Janson et al. |
| 6,039,761 A | 3/2000 | Li et al. |
| 6,039,762 A | 3/2000 | McKay |
| 6,096,080 A | 8/2000 | Nicholson et al. |
| 6,113,638 A | 9/2000 | Williams et al. |
| 6,120,503 A | 9/2000 | Michelson |
| 6,152,927 A | 11/2000 | Farris et al. |
| 6,193,721 B1 | 2/2001 | Michelson |
| 6,206,924 B1 | 3/2001 | Timm |
| 6,235,059 B1 | 5/2001 | Benezech et al. |
| 6,241,769 B1 | 6/2001 | Nicholson et al. |
| 6,241,771 B1 | 6/2001 | Gresser et al. |
| 6,293,949 B1 | 9/2001 | Justis et al. |
| 6,325,805 B1 | 12/2001 | Ogilvie et al. |
| 6,336,928 B1 | 1/2002 | Guerin et al. |
| 6,364,880 B1 | 4/2002 | Michelson |
| 6,432,107 B1 | 8/2002 | Ferree |
| 6,447,524 B1 | 9/2002 | Knodel et al. |
| 6,447,546 B1 | 9/2002 | Bramlet et al. |
| 6,447,547 B1 | 9/2002 | Michelson |
| 6,454,769 B2 | 9/2002 | Wagner et al. |
| 6,458,158 B1 | 10/2002 | Anderson et al. |
| 6,471,725 B1 | 10/2002 | Ralph et al. |
| 6,485,521 B1 | 11/2002 | Say et al. |
| 6,503,250 B2 | 1/2003 | Paul |
| 6,533,786 B1 | 3/2003 | Needham et al. |
| 6,533,818 B1 | 3/2003 | Weber et al. |
| 6,547,823 B2 | 4/2003 | Scarborough et al. |
| 6,569,201 B2 | 5/2003 | Moumene et al. |
| 6,572,654 B1 | 6/2003 | Santilli |
| 6,582,468 B1 | 6/2003 | Gauchet |
| 6,602,255 B1 | 8/2003 | Campbell et al. |
| 6,623,525 B2 | 9/2003 | Ralph et al. |
| 6,673,075 B2 | 1/2004 | Santilli |
| 6,679,887 B2 | 1/2004 | Nicholson et al. |
| 6,716,245 B2 | 4/2004 | Pasquet et al. |
| 6,726,720 B2 | 4/2004 | Ross et al. |
| 6,740,118 B2 | 5/2004 | Eisermann et al. |
| 6,740,186 B2 | 5/2004 | Hawkins et al. |
| 6,743,256 B2 | 6/2004 | Mason |
| 6,767,367 B1 | 7/2004 | Michelson |
| 6,790,233 B2 | 9/2004 | Brodke et al. |
| 6,800,093 B2 | 10/2004 | Nicholson et al. |
| 6,843,805 B2 | 1/2005 | Webb et al. |
| 6,863,689 B2 | 3/2005 | Ralph et al. |
| 6,890,335 B2 | 5/2005 | Grabowski et al. |
| 6,890,355 B2 | 5/2005 | Michelson |
| 6,945,448 B2 | 9/2005 | Medlin et al. |
| 6,970,233 B2 | 11/2005 | Blatchford |
| 7,044,972 B2 | 5/2006 | Mathys, Jr. et al. |
| 7,048,766 B2 | 5/2006 | Ferree |
| 7,056,344 B2 | 6/2006 | Huppert et al. |
| 7,056,345 B2 | 6/2006 | Kuslich |
| 7,060,097 B2 | 6/2006 | Fraser et al. |
| 7,118,580 B1 | 10/2006 | Beyersdorff et al. |
| 7,128,761 B2 | 10/2006 | Kuras et al. |
| 7,135,042 B2 | 11/2006 | Stoll |
| 7,169,150 B2 | 1/2007 | Shipp et al. |
| 7,204,852 B2 | 4/2007 | Marnay et al. |
| 7,235,101 B2 | 6/2007 | Berry et al. |
| 7,238,203 B2 | 7/2007 | Bagga et al. |
| 7,241,313 B2 | 7/2007 | Unwin et al. |
| 7,255,713 B2 | 8/2007 | Malek |
| 7,278,997 B1 | 10/2007 | Mueller et al. |
| 7,303,564 B2 | 12/2007 | Freid et al. |
| 7,320,707 B2 | 1/2008 | Zucherman et al. |
| 7,331,995 B2 | 2/2008 | Eisermann et al. |
| 7,364,589 B2 | 4/2008 | Eisermann |
| 7,497,876 B2 | 3/2009 | Tuke et al. |
| 7,500,976 B2 | 3/2009 | Suh |
| 7,501,073 B2 | 3/2009 | Wen et al. |
| 7,503,934 B2 | 3/2009 | Eisermann et al. |
| 7,503,935 B2 | 3/2009 | Zucherman et al. |
| 7,537,664 B2 | 5/2009 | O'Neill et al. |
| 7,563,284 B2 | 7/2009 | Coppes et al. |
| 7,588,600 B2 | 9/2009 | Benzel et al. |
| 7,594,931 B2 | 9/2009 | Louis et al. |
| 7,611,538 B2 | 11/2009 | Belliard et al. |
| 7,625,375 B2 | 12/2009 | Garden et al. |
| 7,635,447 B2 | 12/2009 | Hamman et al. |
| 7,658,766 B2 | 2/2010 | Melkent et al. |
| 7,662,186 B2 | 2/2010 | Bagga et al. |
| 7,670,359 B2 | 3/2010 | Yundt |
| 7,670,375 B2 | 3/2010 | Schaller |
| 7,686,806 B2 | 3/2010 | Rhyne |
| 7,695,516 B2 | 4/2010 | Zeegers |
| 7,749,271 B2 | 7/2010 | Fischer et al. |
| 7,763,076 B2 | 7/2010 | Navarro et al. |
| 7,766,947 B2 | 8/2010 | Hawkes et al. |
| 7,842,088 B2 | 11/2010 | Rashbaum et al. |
| 7,857,839 B2 | 12/2010 | Duong et al. |
| 7,862,597 B2 | 1/2011 | Gause et al. |
| 7,883,661 B2 | 2/2011 | Hamman et al. |
| 7,896,919 B2 | 3/2011 | Belliard et al. |
| 7,918,382 B2 | 4/2011 | Charlebois et al. |
| 7,922,765 B2 | 4/2011 | Reiley |
| 8,021,403 B2 | 9/2011 | Wall et al. |
| 8,034,076 B2 | 10/2011 | Criscuolo et al. |

(56) References Cited

U.S. PATENT DOCUMENTS

| | | |
|---|---|---|
| 8,043,346 B2 | 10/2011 | Markworth |
| 8,083,796 B1 | 12/2011 | Raiszadeh et al. |
| 8,092,499 B1 | 1/2012 | Roth |
| 8,100,974 B2 | 1/2012 | Duggal et al. |
| 8,105,366 B2 | 1/2012 | Null et al. |
| 8,123,808 B2 | 2/2012 | Dewey et al. |
| 8,147,861 B2 | 4/2012 | Jones et al. |
| 8,162,950 B2 | 4/2012 | Digeser et al. |
| 8,167,946 B2 | 5/2012 | Michelson |
| 8,191,760 B2 | 6/2012 | Charlebois et al. |
| 8,202,305 B2 | 6/2012 | Reiley |
| 8,231,676 B2 | 7/2012 | Trudeau et al. |
| 8,236,034 B2 | 8/2012 | Binder et al. |
| 8,262,737 B2 | 9/2012 | Bagga et al. |
| 8,266,780 B2 | 9/2012 | Bollinger et al. |
| 8,268,100 B2 | 9/2012 | O'Neill et al. |
| 8,303,879 B2 | 11/2012 | Bertele et al. |
| 8,308,805 B2 | 11/2012 | Lynn et al. |
| 8,343,224 B2 | 1/2013 | Lynn et al. |
| 8,349,015 B2 | 1/2013 | Bae et al. |
| 8,350,186 B2 | 1/2013 | Jones et al. |
| 8,361,126 B2 | 1/2013 | Perrow et al. |
| 8,361,150 B2 | 1/2013 | Zhang et al. |
| 8,361,153 B2 | 1/2013 | Ralph et al. |
| 8,361,380 B2 | 1/2013 | Hamman et al. |
| 8,388,663 B2 | 3/2013 | Bush, Jr. et al. |
| 8,388,667 B2 | 3/2013 | Reiley et al. |
| 8,403,969 B2 | 3/2013 | Wallenstein et al. |
| 8,403,991 B2 | 3/2013 | Ullrich, Jr. et al. |
| 8,414,648 B2 | 4/2013 | Reiley |
| 8,414,650 B2 | 4/2013 | Bertele et al. |
| 8,414,651 B2 | 4/2013 | Tyber et al. |
| 8,414,654 B1 | 4/2013 | Ganey |
| 8,414,820 B2 | 4/2013 | Bertele et al. |
| 8,419,777 B2 | 4/2013 | Walker et al. |
| 8,425,570 B2 | 4/2013 | Reiley |
| 8,425,604 B2 | 4/2013 | Trieu |
| 8,430,930 B2 | 4/2013 | Hunt |
| 8,435,301 B2 | 5/2013 | Gerber et al. |
| 8,435,302 B2 | 5/2013 | Ulrich, Jr. et al. |
| 8,444,693 B2 | 5/2013 | Reiley |
| 8,470,004 B2 | 6/2013 | Reiley |
| 8,470,042 B2 | 6/2013 | Zhang et al. |
| 8,480,749 B2 | 7/2013 | Ullrich, Jr. et al. |
| 8,486,115 B2 | 7/2013 | Fisher et al. |
| 8,496,710 B2 | 7/2013 | Bagga et al. |
| 8,500,782 B2 | 8/2013 | Kovach et al. |
| 8,500,811 B2 | 8/2013 | Blain et al. |
| 8,500,819 B2 | 8/2013 | Meridew et al. |
| 8,530,560 B2 | 9/2013 | Kerr et al. |
| 8,535,354 B2 | 9/2013 | Cummins |
| 8,545,568 B2 | 10/2013 | Ulrich, Jr. et al. |
| 8,551,173 B2 | 10/2013 | Lechmann et al. |
| 8,551,176 B2 | 10/2013 | Ullrich, Jr. et al. |
| 8,556,944 B2 | 10/2013 | Dube et al. |
| 8,556,981 B2 | 10/2013 | Jones et al. |
| 8,562,684 B2 | 10/2013 | Ullrich, Jr. et al. |
| 8,562,685 B2 | 10/2013 | Ullrich, Jr. et al. |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,590 B2 | 11/2013 | Ullrich, Jr. et al. |
| 8,617,246 B2 | 12/2013 | Malone |
| 8,617,248 B2 | 12/2013 | Ullrich, Jr. et al. |
| 8,632,604 B2 | 1/2014 | Brooks |
| 8,636,803 B2 | 1/2014 | Hibri et al. |
| 8,663,332 B1 | 3/2014 | To et al. |
| 8,668,723 B2 | 3/2014 | Altarac et al. |
| 8,673,016 B2 | 3/2014 | Liu |
| 8,709,088 B2 | 4/2014 | Kleiner et al. |
| 8,727,387 B2 | 5/2014 | Knapp |
| 8,734,462 B2 | 5/2014 | Reiley et al. |
| 8,747,412 B2 | 6/2014 | Bae et al. |
| 8,758,442 B2 | 6/2014 | Ullrich, Jr. et al. |
| 8,758,443 B2 | 6/2014 | Ullrich, Jr. et al. |
| 8,814,939 B2 | 8/2014 | Ullrich, Jr. et al. |
| 8,814,978 B2 | 8/2014 | Hamman et al. |
| 8,821,555 B2 | 9/2014 | Bae et al. |
| 8,827,986 B2 | 9/2014 | Shachar et al. |
| 8,834,571 B2 | 9/2014 | Bagga et al. |
| 8,840,623 B2 | 9/2014 | Reiley |
| 8,845,736 B2 | 9/2014 | Zhang et al. |
| 8,864,831 B2 | 10/2014 | Lee et al. |
| 8,870,957 B2 | 10/2014 | Vraney et al. |
| 8,900,277 B2 | 12/2014 | Perrow et al. |
| 8,906,077 B2 | 12/2014 | Bush, Jr. et al. |
| 8,906,093 B2 | 12/2014 | Malone |
| 8,906,095 B2 | 12/2014 | Christensen et al. |
| 8,940,053 B2 | 1/2015 | Ullrich, Jr. et al. |
| 8,979,934 B2 | 3/2015 | Kirschman |
| 8,985,430 B2 | 3/2015 | Charlebois et al. |
| 8,992,619 B2 | 3/2015 | Patterson et al. |
| 9,060,876 B1 | 6/2015 | To et al. |
| 9,078,718 B2 | 7/2015 | Campbell |
| 9,089,428 B2 | 7/2015 | Bertele et al. |
| 9,135,374 B2 | 9/2015 | Jones et al. |
| 9,138,275 B2 | 9/2015 | Bae et al. |
| 9,138,276 B2 | 9/2015 | Bae et al. |
| 9,180,010 B2 | 11/2015 | Dong et al. |
| 9,320,549 B2 | 4/2016 | Fraser et al. |
| 9,351,775 B2 | 5/2016 | Bush, Jr. et al. |
| 9,375,237 B2 | 6/2016 | Keegan et al. |
| 9,381,044 B2 | 7/2016 | Robinson et al. |
| 9,387,087 B2 | 7/2016 | Tyber |
| 9,615,733 B2 | 4/2017 | Nottmeier |
| 9,629,664 B2 | 4/2017 | Altarac et al. |
| 9,655,665 B2 | 5/2017 | Perrow |
| 9,730,807 B2 | 8/2017 | Donaldson |
| 9,782,270 B2 | 10/2017 | Wickham |
| 9,788,968 B2 | 10/2017 | Bae et al. |
| 9,925,051 B2 | 3/2018 | Bae et al. |
| 10,070,970 B2 | 9/2018 | Lynn et al. |
| 10,835,388 B2 * | 11/2020 | Milz ............... A61F 2/447 |
| 2002/0004683 A1 | 1/2002 | Michelson |
| 2002/0035400 A1 | 3/2002 | Bryan et al. |
| 2002/0165613 A1 | 11/2002 | Lin et al. |
| 2003/0045940 A1 | 3/2003 | Eberlein et al. |
| 2003/0055505 A1 | 3/2003 | Sicotte et al. |
| 2003/0083748 A1 | 5/2003 | Lee et al. |
| 2003/0195517 A1 | 10/2003 | Michelson |
| 2003/0195632 A1 | 10/2003 | Foley et al. |
| 2004/0059318 A1 | 3/2004 | Zhang et al. |
| 2004/0117022 A1 | 6/2004 | Marnay et al. |
| 2004/0122426 A1 | 6/2004 | Michelson |
| 2004/0133279 A1 | 7/2004 | Krueger et al. |
| 2004/0148028 A1 | 7/2004 | Ferree et al. |
| 2004/0176853 A1 | 9/2004 | Sennett et al. |
| 2004/0181226 A1 | 9/2004 | Michelson |
| 2004/0193269 A1 | 9/2004 | Fraser et al. |
| 2004/0193271 A1 | 9/2004 | Fraser et al. |
| 2004/0199254 A1 | 10/2004 | Louis et al. |
| 2004/0204712 A1 | 10/2004 | Kolb et al. |
| 2004/0210218 A1 | 10/2004 | Dixon et al. |
| 2004/0215195 A1 | 10/2004 | Shipp et al. |
| 2004/0220566 A1 | 11/2004 | Bray |
| 2004/0220571 A1 | 11/2004 | Assaker et al. |
| 2004/0220668 A1 | 11/2004 | Eisermann et al. |
| 2004/0220670 A1 | 11/2004 | Eisermann et al. |
| 2004/0225360 A1 | 11/2004 | Malone |
| 2004/0230307 A1 | 11/2004 | Eisermann |
| 2004/0258732 A1 | 12/2004 | Shikinami |
| 2004/0260286 A1 | 12/2004 | Ferree |
| 2005/0004672 A1 | 1/2005 | Pafford et al. |
| 2005/0033294 A1 | 2/2005 | Garden et al. |
| 2005/0033435 A1 | 2/2005 | Belliard et al. |
| 2005/0043802 A1 | 2/2005 | Eisermann et al. |
| 2005/0049593 A1 | 3/2005 | Duong et al. |
| 2005/0049595 A1 | 3/2005 | Suh et al. |
| 2005/0060034 A1 | 3/2005 | Berry et al. |
| 2005/0070900 A1 | 3/2005 | Serhan et al. |
| 2005/0075633 A1 | 4/2005 | Ross |
| 2005/0123672 A1 | 6/2005 | Justin et al. |
| 2005/0143820 A1 | 6/2005 | Zucherman et al. |
| 2005/0149192 A1 | 7/2005 | Zucherman et al. |

(56) References Cited

U.S. PATENT DOCUMENTS

| | | |
|---|---|---|
| 2005/0149193 A1 | 7/2005 | Zucherman et al. |
| 2005/0154460 A1 | 7/2005 | Yundt |
| 2005/0165408 A1 | 7/2005 | Puno et al. |
| 2005/0177238 A1 | 8/2005 | Khandkar et al. |
| 2005/0192586 A1 | 9/2005 | Zucherman et al. |
| 2005/0216081 A1 | 9/2005 | Taylor |
| 2006/0004453 A1 | 1/2006 | Bartish et al. |
| 2006/0036250 A1 | 2/2006 | Lange et al. |
| 2006/0085071 A1 | 4/2006 | Lechmann et al. |
| 2006/0089656 A1 | 4/2006 | Allard et al. |
| 2006/0116769 A1 | 6/2006 | Marnay et al. |
| 2006/0116770 A1 | 6/2006 | White et al. |
| 2006/0122603 A1 | 6/2006 | Kolb |
| 2006/0129238 A1 | 6/2006 | Paltzer |
| 2006/0136063 A1 | 6/2006 | Zeegers |
| 2006/0147332 A1 | 7/2006 | Jones et al. |
| 2006/0178745 A1 | 8/2006 | Bartish et al. |
| 2006/0195097 A1 | 8/2006 | Evans et al. |
| 2006/0212121 A1 | 9/2006 | Ferree |
| 2006/0293668 A1 | 12/2006 | May et al. |
| 2007/0050032 A1 | 3/2007 | Gittings et al. |
| 2007/0050033 A1 | 3/2007 | Reo et al. |
| 2007/0055378 A1 | 3/2007 | Ankney et al. |
| 2007/0073404 A1 | 3/2007 | Rashbaum et al. |
| 2007/0118145 A1 | 5/2007 | Fischer et al. |
| 2007/0123884 A1 | 5/2007 | Abdou |
| 2007/0123985 A1 | 5/2007 | Errico et al. |
| 2007/0142914 A1 | 6/2007 | Jones et al. |
| 2007/0173816 A1 | 7/2007 | Metz-Stavenhagen |
| 2007/0173940 A1 | 7/2007 | Hestad et al. |
| 2007/0179609 A1 | 8/2007 | Goble et al. |
| 2007/0233244 A1 | 10/2007 | Lopez et al. |
| 2007/0233261 A1 | 10/2007 | Lopez et al. |
| 2007/0239278 A1 | 10/2007 | Heinz |
| 2007/0270968 A1 | 11/2007 | Baynham et al. |
| 2008/0004709 A1 | 1/2008 | O'Neill et al. |
| 2008/0015702 A1 | 1/2008 | Lakin et al. |
| 2008/0051901 A1 | 2/2008 | de Villiers et al. |
| 2008/0051902 A1 | 2/2008 | Dwyer |
| 2008/0097435 A1 | 4/2008 | DeRidder et al. |
| 2008/0109005 A1 | 5/2008 | Trudeau et al. |
| 2008/0154377 A1 | 6/2008 | Voellmicke |
| 2008/0161927 A1 | 7/2008 | Savage et al. |
| 2008/0183292 A1 | 7/2008 | Trieu |
| 2008/0249575 A1 | 10/2008 | Waugh et al. |
| 2008/0262623 A1 | 10/2008 | Bagga et al. |
| 2008/0269756 A1 | 10/2008 | Tomko et al. |
| 2008/0306595 A1 | 12/2008 | McLeod et al. |
| 2009/0005870 A1 | 1/2009 | Hawkins et al. |
| 2009/0088849 A1 | 4/2009 | Armstrong et al. |
| 2009/0093885 A1 | 4/2009 | Levieux et al. |
| 2009/0105832 A1 | 4/2009 | Allain et al. |
| 2009/0112323 A1 | 4/2009 | Hestad et al. |
| 2009/0138015 A1 | 5/2009 | Conner et al. |
| 2009/0164020 A1 | 6/2009 | Janowski et al. |
| 2009/0198184 A1 | 8/2009 | Martin et al. |
| 2009/0240333 A1 | 9/2009 | Trudeau et al. |
| 2009/0287257 A1 | 11/2009 | Hagen |
| 2009/0306717 A1 | 12/2009 | Kercher et al. |
| 2010/0004747 A1 | 1/2010 | Lin |
| 2010/0042218 A1 | 2/2010 | Nebosky et al. |
| 2010/0042221 A1 | 2/2010 | Boyd |
| 2010/0076559 A1 | 3/2010 | Bagga et al. |
| 2010/0094426 A1 | 4/2010 | Grohowski, Jr. et al. |
| 2010/0137916 A1 | 6/2010 | Hynes et al. |
| 2010/0137990 A1 | 6/2010 | Apatsidis et al. |
| 2010/0185292 A1 | 7/2010 | Hochschuler et al. |
| 2010/0211119 A1 | 8/2010 | Refai et al. |
| 2010/0222750 A1 | 9/2010 | Cheng |
| 2010/0256773 A1 | 10/2010 | Thijs et al. |
| 2010/0262244 A1 | 10/2010 | Savage-Erickson et al. |
| 2010/0262245 A1 | 10/2010 | Alfaro et al. |
| 2010/0268343 A1 | 10/2010 | Dewey et al. |
| 2011/0004256 A1 | 1/2011 | Biedermann et al. |
| 2011/0004307 A1 | 1/2011 | Ahn et al. |
| 2011/0029081 A1 | 2/2011 | Malone |
| 2011/0071635 A1 | 3/2011 | Zhang et al. |
| 2011/0092948 A1 | 4/2011 | Shachar et al. |
| 2011/0106159 A1 | 5/2011 | Nazeck |
| 2011/0160866 A1 | 6/2011 | Laurence et al. |
| 2011/0196494 A1 | 8/2011 | Yedlicka et al. |
| 2011/0196495 A1 | 8/2011 | Hunt |
| 2011/0224796 A1 | 9/2011 | Weiland et al. |
| 2011/0282392 A1 | 11/2011 | Murphy et al. |
| 2011/0282454 A1 | 11/2011 | Ullrich, Jr. et al. |
| 2011/0301709 A1 | 12/2011 | Kraus et al. |
| 2011/0313532 A1 | 12/2011 | Hunt |
| 2012/0029432 A1 | 2/2012 | Sweeney |
| 2012/0071933 A1 | 3/2012 | DeRidder |
| 2012/0078315 A1 | 3/2012 | Sweeney |
| 2012/0078371 A1 | 3/2012 | Gamache et al. |
| 2012/0078373 A1 | 3/2012 | Gamache et al. |
| 2012/0123544 A1 | 5/2012 | Suh et al. |
| 2012/0215315 A1 | 8/2012 | Hochschuler et al. |
| 2012/0253406 A1 | 10/2012 | Bae et al. |
| 2012/0265306 A1 | 10/2012 | Trieu |
| 2012/0277876 A1 | 11/2012 | Ullrich, Jr. et al. |
| 2012/0303127 A1 | 11/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0330420 A1 | 12/2012 | Brodke et al. |
| 2013/0030529 A1 | 1/2013 | Hunt |
| 2013/0123925 A1 | 5/2013 | Patterson et al. |
| 2013/0123935 A1 | 5/2013 | Hunt et al. |
| 2013/0158672 A1 | 6/2013 | Hunt |
| 2013/0184822 A1 | 7/2013 | Kleiner |
| 2013/0218282 A1 | 8/2013 | Hunt |
| 2013/0226302 A1 | 8/2013 | Bae et al. |
| 2013/0274886 A1 | 10/2013 | Matsumoto et al. |
| 2013/0282122 A1 | 10/2013 | Ullrich, Jr. et al. |
| 2013/0292357 A1 | 11/2013 | Ullrich, Jr. et al. |
| 2013/0304218 A1 | 11/2013 | Ullrich, Jr. et al. |
| 2013/0306591 A1 | 11/2013 | Ullrich, Jr. et al. |
| 2013/0338777 A1 | 12/2013 | Bagga et al. |
| 2014/0025169 A1 | 1/2014 | Lechmann et al. |
| 2014/0031942 A1 | 1/2014 | Ullrich, Jr. et al. |
| 2014/0046449 A1 | 2/2014 | Ullrich, Jr. et al. |
| 2014/0052258 A1 | 2/2014 | Ball et al. |
| 2014/0114415 A1 | 4/2014 | Tyber |
| 2014/0114421 A1 | 4/2014 | Ullrich, Jr. et al. |
| 2014/0121776 A1 | 5/2014 | Hunt |
| 2014/0128924 A1 | 5/2014 | Perrow et al. |
| 2014/0200670 A1 | 7/2014 | Chin et al. |
| 2014/0277461 A1 | 9/2014 | Nebosky et al. |
| 2014/0277464 A1 | 9/2014 | Richter et al. |
| 2014/0277482 A1 | 9/2014 | Gfeller et al. |
| 2014/0277491 A1 | 9/2014 | Fang et al. |
| 2014/0277511 A1 | 9/2014 | Ullrich, Jr. et al. |
| 2014/0277512 A1 | 9/2014 | Ullrich, Jr. et al. |
| 2014/0288649 A1 | 9/2014 | Hunt |
| 2014/0288650 A1 | 9/2014 | Hunt |
| 2014/0350682 A1 | 11/2014 | Bagga et al. |
| 2015/0012100 A1 | 1/2015 | Ullrich, Jr. et al. |
| 2015/0018956 A1 | 1/2015 | Steinmann et al. |
| 2015/0032220 A1 | 1/2015 | Tyber et al. |
| 2015/0045903 A1 | 2/2015 | Neal |
| 2015/0073422 A1 | 3/2015 | Chegini et al. |
| 2015/0157465 A1 | 6/2015 | Kirschman |
| 2015/0202047 A1 | 7/2015 | Patterson et al. |
| 2015/0202051 A1 | 7/2015 | Tanaka et al. |
| 2015/0230832 A1 | 8/2015 | Fraser et al. |
| 2016/0038301 A1 | 2/2016 | Wickham |
| 2016/0081818 A1 | 3/2016 | Waugh et al. |
| 2016/0199190 A1 | 7/2016 | Sharifi-Mehr et al. |
| 2016/0199193 A1 | 7/2016 | Willis et al. |
| 2017/0049491 A1 | 2/2017 | Ross et al. |
| 2017/0119537 A1 | 5/2017 | Tepper et al. |
| 2017/0182222 A1 | 6/2017 | Paddock et al. |
| 2017/0224388 A1 | 8/2017 | Walker et al. |
| 2017/0238974 A1 | 8/2017 | Konieczynski et al. |
| 2019/0008655 A1 | 1/2019 | Body |
| 2019/0083270 A1* | 3/2019 | Milz .......... A61F 2/447 |
| 2021/0038404 A1* | 2/2021 | Milz .......... A61F 2/447 |

(56) References Cited

U.S. PATENT DOCUMENTS

FOREIGN PATENT DOCUMENTS

| EP | 0179695 A1 | 4/1986 |
|---|---|---|
| EP | 0505634 A1 | 9/1992 |
| EP | 1327423 A1 | 7/2003 |
| EP | 1790298 A1 | 5/2007 |
| EP | 1872746 A2 | 1/2008 |
| FR | 2858546 A1 | 2/2005 |
| JP | H08503876 A | 4/1996 |
| WO | 03005939 A2 | 1/2003 |
| WO | 03039400 A2 | 5/2003 |
| WO | 03053290 A1 | 7/2003 |
| WO | 2003092507 A2 | 11/2003 |
| WO | 2004071359 A1 | 8/2004 |
| WO | 2004080355 A1 | 9/2004 |
| WO | 2004108015 A2 | 12/2004 |
| WO | 2005051243 A2 | 6/2005 |
| WO | 2005071190 A2 | 8/2005 |
| WO | 2006033067 A3 | 3/2006 |
| WO | 2006051547 A2 | 5/2006 |
| WO | 2006074414 A2 | 7/2006 |
| WO | 2006086494 A2 | 8/2006 |
| WO | 2006121795 A2 | 11/2006 |
| WO | 2007028098 A2 | 3/2007 |
| WO | 2007087366 A2 | 8/2007 |
| WO | 2008014453 A2 | 1/2008 |
| WO | 2008021955 A2 | 2/2008 |
| WO | 2009099559 A2 | 8/2009 |
| WO | 2010021612 A1 | 2/2010 |
| WO | 2010028045 A1 | 3/2010 |
| WO | 2010052283 A1 | 5/2010 |
| WO | 2010121149 A2 | 10/2010 |
| WO | 2013133729 A1 | 9/2013 |
| WO | 2014018325 A1 | 1/2014 |

OTHER PUBLICATIONS

Australian Examination Report for AU2017216532 dated Oct. 23, 2018.
Bobyn JD. Next generation porous metals forbiologic fixation. In: Glassman AH, Lachiewicz PF, Tanzer, M, eds. Orthopaedic Knowledge Update: Hip and Knee Reconstruction 4. Rosemont, IL: American Academy of Orthopaedic Surgeons; 2011:45-58.
Bobyn, J. D., G. J. Stackpool, S. A. Hacking, M. Tanzer, and J. J. Krygier. "Characteristics of Bone Ingrowth and Interface Mechanics of a New Porous Tantalum Biomaterial." The Journal of Bone and Joint Surgery81.5 (1999): 907-14.
Callaghan, J. J. (1993). "The clinical results and basic science of total hip arthroplasty with porous-coated prostheses." J Bone Joint Surg Am 75(2): 299-310.
Charles L. Bush, U.S. Appl. No. 62/653,877, filed Apr. 6, 2018, titled "Faceted Bone Plate".
European Search Report for U.S. Appl. No. 16/170,075 dated Oct. 21, 2016.
European Search Report dated Sep. 26, 2012 for PCT/US2010022494.
Extended European Search Report for U.S. Appl. No. 14/152,779 dated Mar. 18, 2014.
Extended European Search Report for Application No. 15161713.1 dated Jun. 29, 2015.
Extended European Search Report for Application No. 16151374.2 dated Jun. 8, 2016.
Extended European Search Report for U.S. Appl. No. 16/151,375 dated Jun. 8, 2016.
Extended European Search Report for Application No. EP16171066 dated Dec. 14, 2016.
Extended European Search Report for Application No. EP16189379 dated Jun. 6, 2017.
Extended European Search Report for Application No. EP16202603 dated May 31, 2017.
Harris, W. H. and M. Jasty (1985). "Bone ingrowth into porous coated canine acetabular replacements: the effect of pore size, apposition, and dislocation." Hip: 214-34.
International Search Report and Writen Opinion, PCT/US2010/044988, dated Feb. 4, 2011.
International Search Report and Written Opinion for Application No. PCT/US2010/055259, dated Apr. 7, 2011.
International Search Report and Written Opinion, PCT/US2010/22494, dated Oct. 25, 2010.
Karageorgiou, V., and D. Kaplan. "Porosity of 3D Biomaterial Scaffolds and Osteogenesis", Biomaterials 26.27 (2005): 5474-491.
Kujala, S. et al. (2003): "Effect of porosity on the osteointegration and bone ingrowth of a weightbearing nickel-titanium bone graft substitute", Biomaterials, 24(25), Nov. 2003, pp. 4691-4697.
Sharifi-Mehr et al., U.S. Appl. No. 14/994,697, filed Jan. 13, 2016.
Willis et al., U.S. Appl. No. 14/994,749, filed Jan. 13, 2016.
Wu, s et al (2013). Porous Ti6Al4V Cage Has Better Osseointegration and Less Micromotion Than a PEEK cage in Sheep Vertebral Fusion. Artificial organs 37(12).

* cited by examiner

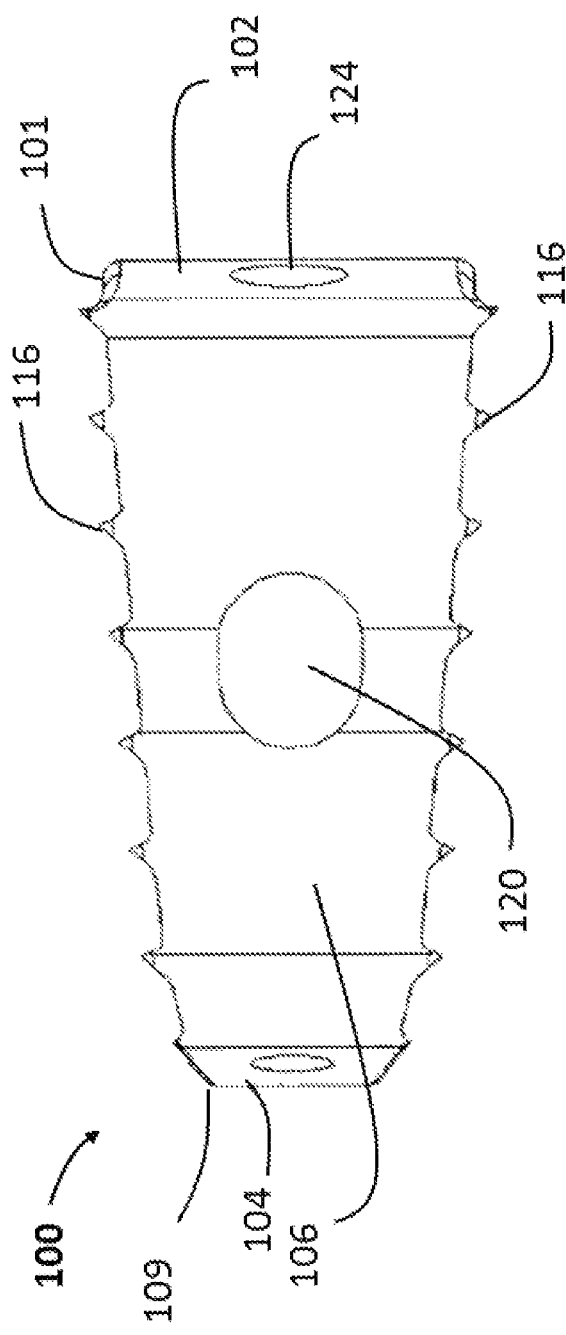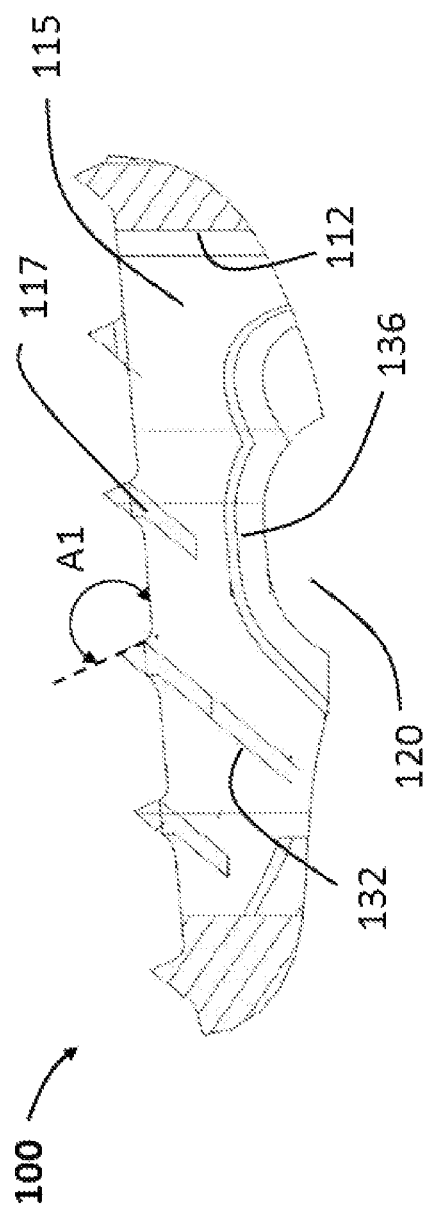

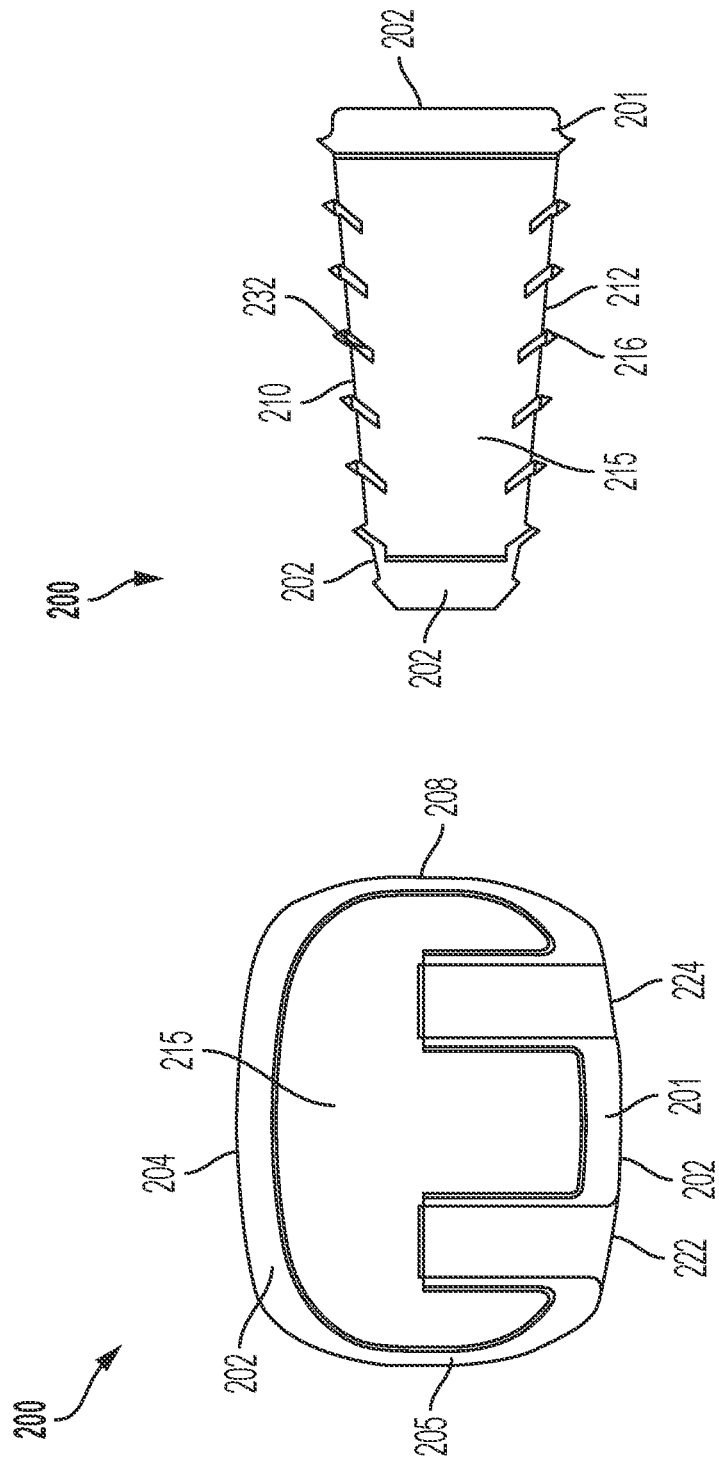

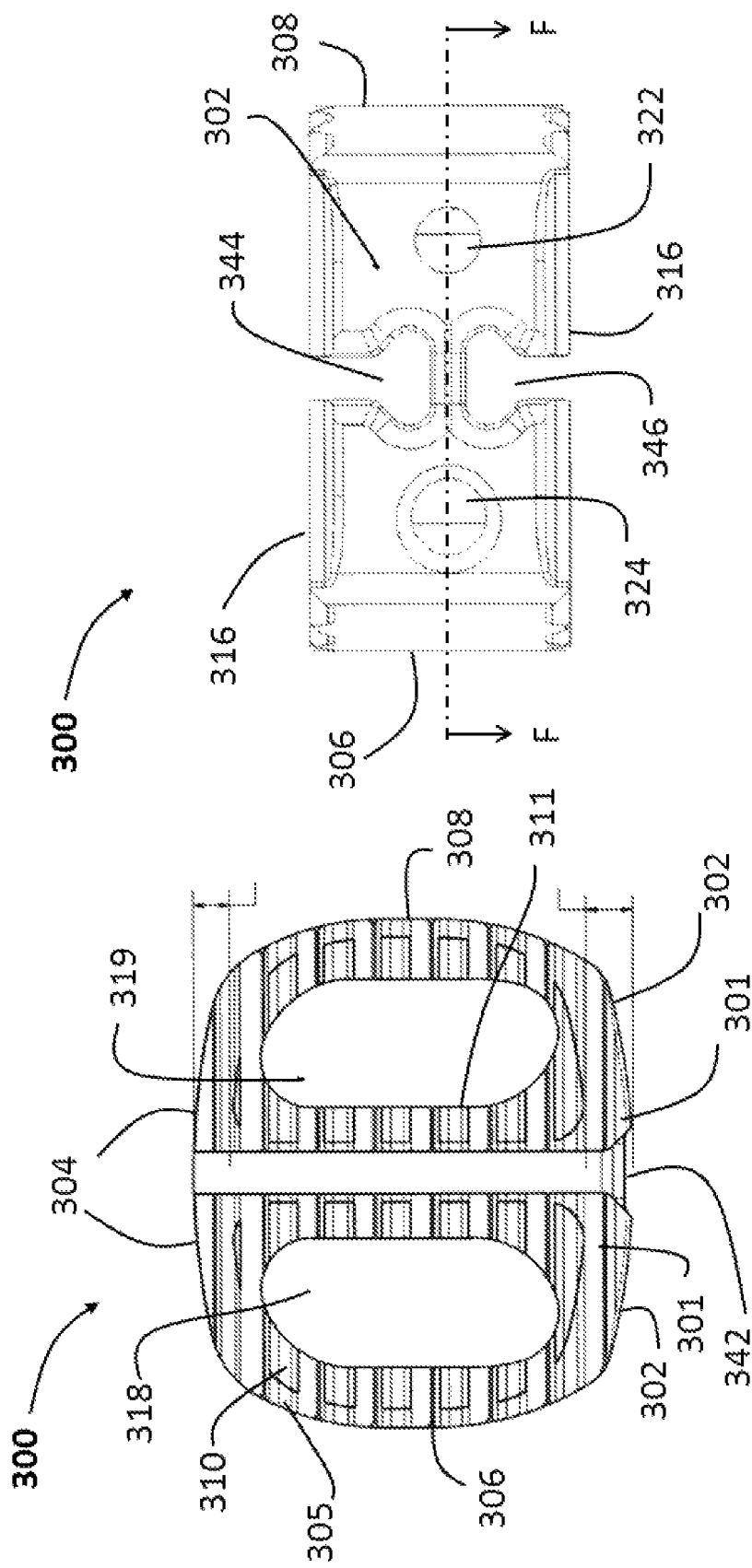

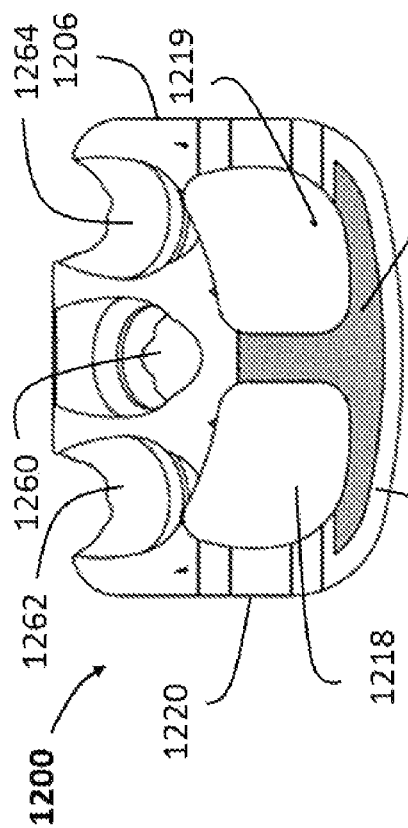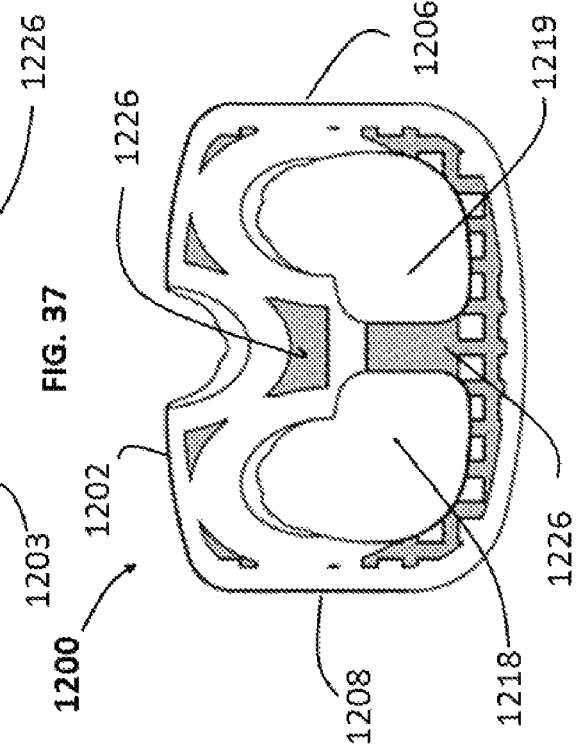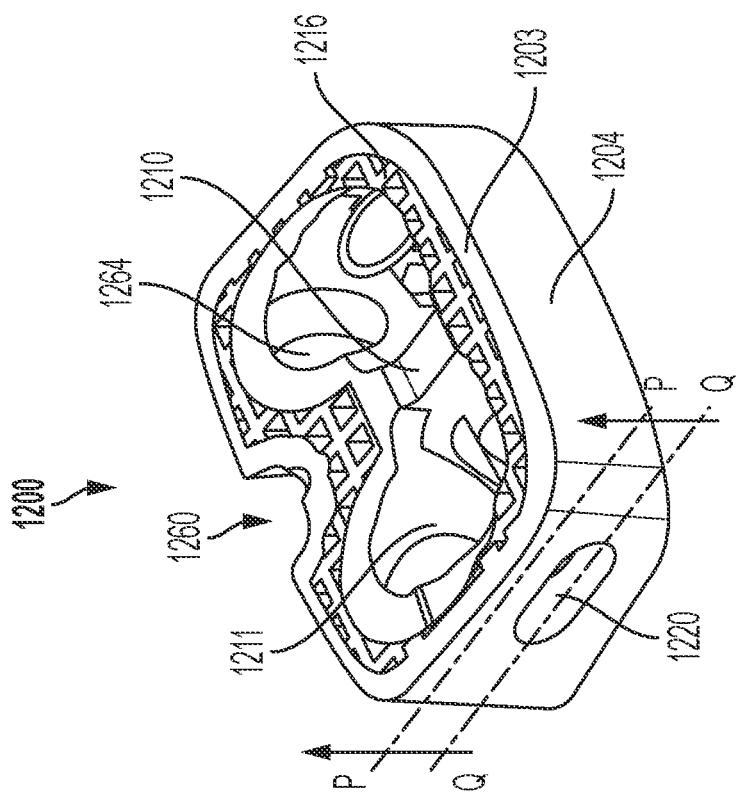
FIG. 37
FIG. 38
FIG. 36

SPINAL IMPLANTS

CROSS-REFERENCE TO RELATED APPLICATION

This application is a continuation of U.S. patent application Ser. No. 16/135,432, filed on Sep. 19, 2018, which claims the benefit of the filing date of U.S. Provisional Patent Application No. 62/560,910, filed on Sep. 20, 2017, the disclosures of which are hereby incorporated by reference.

BACKGROUND OF THE INVENTION

The present invention generally relates to spinal implants and a method of fabricating the same, and in particular, relates to a spinal implant with porous and solid structures and the methods for fabricating them.

Back pain can be caused by many different maladies, not the least of which are problems that directly impact the intervertebral discs of the spine. Typical disc issues include, inter alia, degeneration, bulging, herniation, thinning and abnormal movement. One method of treatment of such disc problems that has been widely utilized in the field of spinal surgery is a spinal fusion procedure, whereby an affected disc is removed and the adjacent vertebral bodies are fused together through the use of interbody spacers, implants or the like. In some instances, it may also be necessary to remove and replace an entire vertebral body. This is often accomplished through the use of a larger implant that acts to fuse together the vertebral bodies adjacent the removed vertebral body.

The aforementioned implants often rely upon mechanical features to ensure engagement between the devices and the bone of the existing vertebral bodies. This coupled with the normal compressive load of the spine acts to keep the implant in place until bone can grow from the existing vertebral bodies into and through the implant. To encourage the bone growth, the implants are often pre-loaded with bone growth promoting material and thereafter placed into the spine. Bone growth promoting material may include naturally occurring bone, artificial materials or the like.

To further ensure a strong implant-bone connection, some existing implants include an area formed of porous material that allows bone to grow into it. Although there is little doubt that the bone growth into the implant is beneficial in maintaining an implant in place, these implants are often very difficult (and thusly, expensive) to manufacture. Additionally, existing implants that implement porous material do so in a limited manner Often times, because of manufacturing or strength concerns or the like, the porous material is limited to a thin layer covering the upper and lower surfaces of the implant, which only allows for a small amount of bone to grow into the implant.

Therefore, there exists a need for an improved spinal implant that provides sufficient porous material, yet maintains the necessary strength required of a spinal implant.

BRIEF SUMMARY OF THE INVENTION

Disclosed herein are implants with solid and porous materials.

In a first aspect of the present invention, a spinal implant with a solid frame and an inner porous layer is provided. The spinal implant may include a solid frame having a medial or first side wall defining a medial or first side wall thickness, a lateral or second side wall defining a lateral or second side wall thickness, a posterior wall defining a posterior wall thickness and an anterior wall defining an anterior wall thickness. A porous inner layer may be disposed within the solid frame. The porous layer may have an exposed superior and an exposed inferior surface. An inner first cavity may extend in a superior-inferior direction and may be defined by the porous inner layer and the solid frame. The solid frame may have one or more ribs extending from the medial wall to the lateral wall above the superior and inferior surface. A porous posterior wall thickness and a porous anterior wall thickness may be less than the posterior wall thickness and the anterior wall thickness respectively. A porous medial wall thickness and porous lateral wall thickness may be greater than the medial wall thickness and the lateral wall thickness respectively.

In accordance with this first aspect, the spinal implant may have two or more inner cavities. Each cavity may extend in a superior-inferior direction and may be defined by the porous inner layer and the solid frame. The spinal implant may have an inner second cavity extending in a superior-inferior direction and may be defined by the porous inner layer and the solid frame. A crossbar may run in medial-lateral direction and separate the two cavities. The crossbar may be defined by the solid frame and may include a window to allow fluid communication between the first and second cavities. The window may be defined by the porous inner layer.

Further in accordance with the first aspect, the lateral wall thickness and the medial wall thickness may be at least 0.25 mm.

Still further in accordance with the first aspect, the lateral wall thickness and the medial wall thickness may vary along an anterior-posterior direction. The wall thickness may have a maximum thickness at the anterior and posterior ends and a minimum thickness in between the anterior and posterior ends.

Still further in accordance with the first aspect, the ribs may have a triangular cross-section, an apex of the triangular cross-section may away from the spinal implant. The ribs may engage with vertebral end plates of a first and a second vertebral body to secure spinal implant between the vertebral bodies. The spinal implant may have one or more cavities extending in a medial-lateral direction. The anterior wall and the posterior wall may include at least one hole to engage with a surgical insertion tool. The inner walls of the hole may be defined by the solid frame.

Still further in accordance with the first aspect, the anterior and posterior walls may include at least one hole in fluid communication with the inner cavity. The inner walls of the hole may be defined by the porous inner layer and the solid frame. The solid frame may be metal. The metal may be titanium.

Still further in accordance with the first aspect, the inner porous layer may have a mean pore diameter between 400 and 500 micron. The spinal implant may be manufactured by an additive manufacturing process.

In a second aspect of the present invention, a spinal implant with a solid frame and an inner porous layer is provided. The spinal implant may have a solid frame with a medial wall, a lateral wall, a posterior wall and an anterior wall. A porous inner layer may be disposed within the solid frame. The porous layer may have an exposed superior and an exposed inferior surface. The solid frame may have one or more ribs extending from the medial wall to the lateral wall above the superior and inferior surface.

In a third aspect of the present invention, an implant assembly is provided. The implant assembly may include an implant and an inserter. The inserter may have a shaft with a proximal end and a distal end with external threading and a post extending distally from a base of the inserter. The post may be parallel to the shaft. The implant may have a first and a second recess. The second recess may be configured to receive the post and the first recess may have internal threading to threadingly engage with the external threading to secure the inserter to the implant.

In a fourth aspect of the present invention, a method of placing a spinal implant using an inserter is provided. The method according to this embodiment may include the steps of placing a distal end of a post of the inserter in a first recess of the spinal implant, securing the spinal implant to the inserter by engaging a distal tip of a shaft of an inserter in a second recess of the spinal implant, placing the spinal implant to a target location using the inserter, and disengaging the post and the shaft of the inserter from the spinal implant.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIG. 6 is a side view of the spinal implant of FIG. 1;

FIG. 7 is a partial side cross-sectional view along line C-C of the spinal implant of FIG. 4;

FIG. 9 is a top cross-sectional view along line D-D of the spinal implant of FIG. 8;

FIG. 10 is a side cross-sectional view along line E-E of the spinal implant of FIG. 8;

FIG. 12 is a top view of the spinal implant of FIG. 11;

FIG. 13 is a front view of the spinal implant of FIG. 11;

FIG. 36 is a top perspective view of a spinal implant according to another embodiment of the present invention;

FIG. 37 is a bottom cross-sectional view along line P-P of the spinal implant of FIG. 36;

FIG. 38 is a bottom cross-sectional view along line Q-Q of the spinal implant of FIG. 36

DETAILED DESCRIPTION

Figure 1:
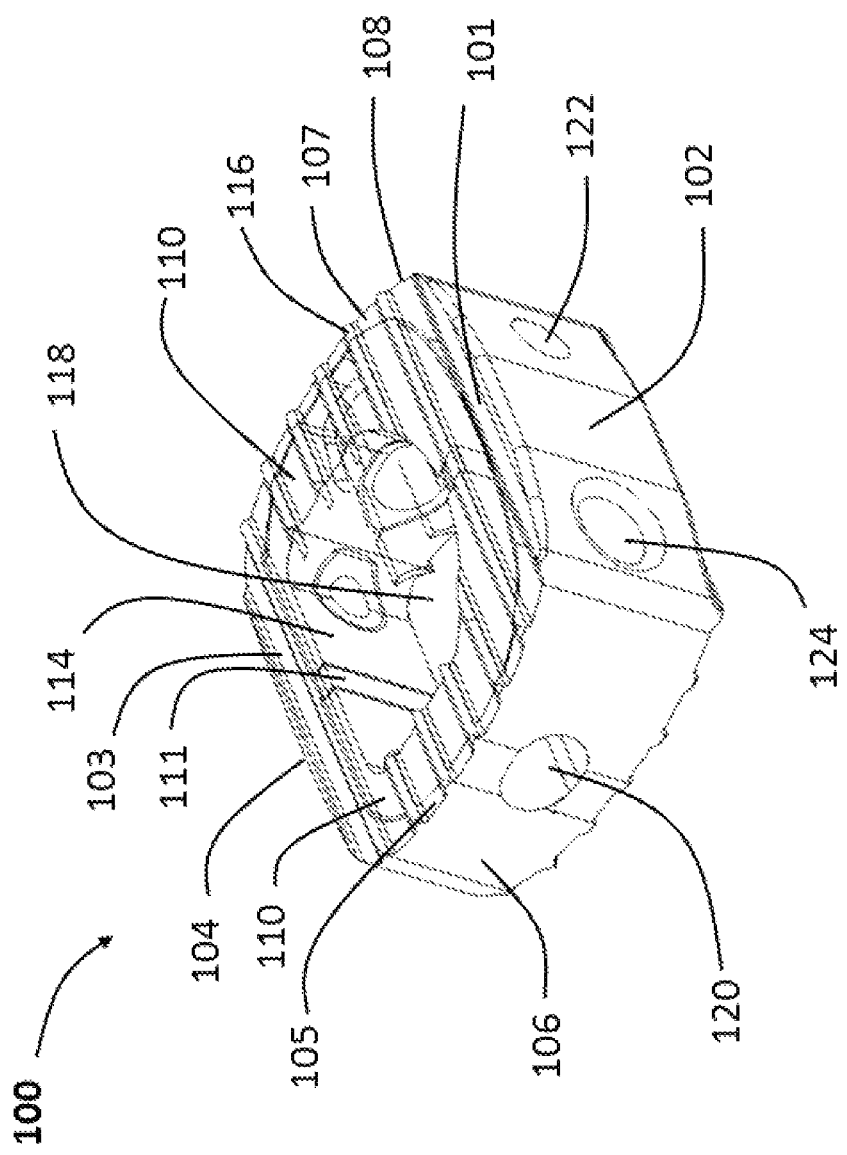
FIG. 1 is a front perspective view of a spinal implant according to an embodiment of the present invention.

Reference will now be made to the embodiments of the present invention illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, when referring to bones or other parts of the body, the term "anterior" means toward the front of the body and the term "posterior" means toward the back of the body. The term "medial" means toward the midline of the body and the term "lateral" means away from the midline of the body. In some instances, embodiments disclosed herein may be located at the midline of the body. In these instances, the term "medial" means toward the left side of the embodiment and the term "lateral" means toward the right side of the embodiment when viewed in an anterior-posterior direction. The term "superior" means closer to the head and the term "inferior" means more distant from the head.

FIGS. 1-7 show a spinal implant 100 according to a first embodiment of the present invention. Spinal implant 100, as shown, is a cervical interbody device with solid and porous structures. Implant 100 can be comprised of a porous metal or have a porous metal surface such as a porous titanium alloy, including Tritanium® by Howmedica Osteonics Corporation. However, as will be readily apparent from the below discussion pertaining to other embodiments, the present invention is not limited to any particular type of implant design. Rather, it is contemplated that certain features of the present invention can be implemented in different types of implants. For instance, implants according to the present invention can be adapted for use in procedures in which implantation from anterior or lateral aspects of the patient, as will be discussed below. Moreover, although disclosed as being constructed of metallic materials, it is contemplated that implants according to the present invention may be constructed of polymeric materials such as PEEK or the like which provide the required rigidity. Additionally, each of the embodiments shown in the drawings are designed for placement between adjacent vertebral bodies, but it is contemplated that implants in accordance with the present invention may be designed for use as vertebral body replacements.

Figure 2:
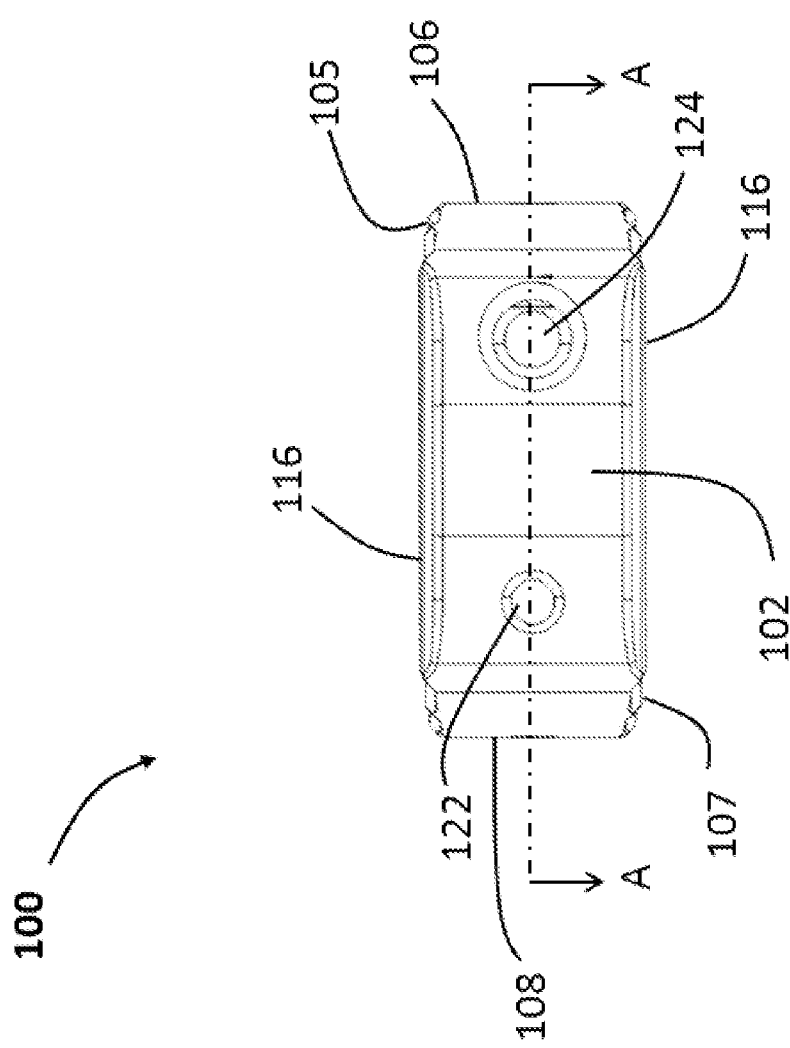
FIG. 2 is a front view of the spinal implant of FIG. 1.
Figure 3:
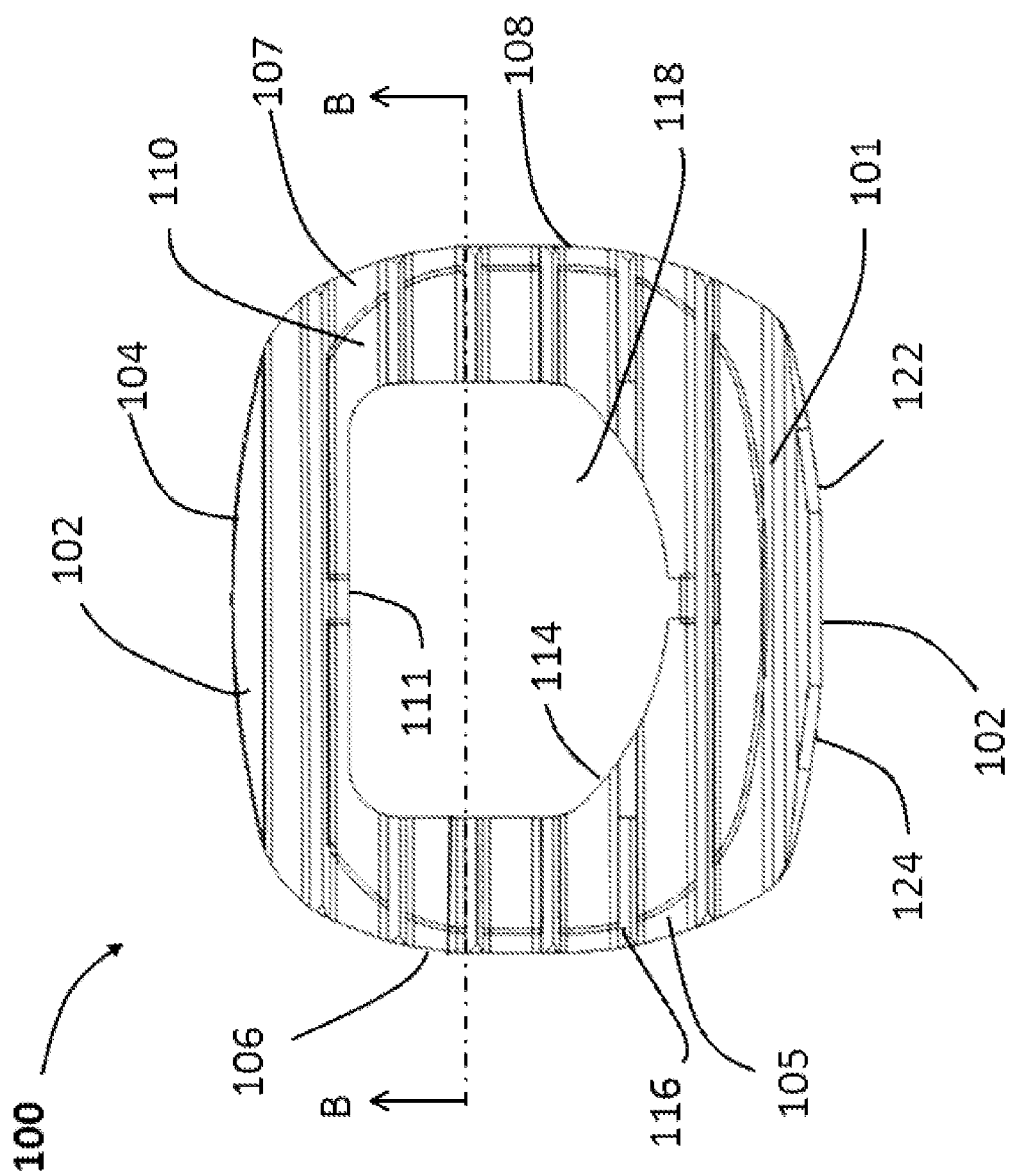
FIG. 3 is a top view of the spinal implant of FIG. 1.

As shown in FIGS. 1-3, spinal implant 100 includes solid peripheral walls and an inner porous layer. The solid peripheral walls include an anterior solid wall 102, a posterior solid wall 104, a medial solid or first side wall 106 and a lateral or second side solid wall 108, that are interconnected to form a unitary wall. As some of the implants disclosed herein are symmetrical and are intended to be situated symmetrically about the midline of the body, the terms "medial" and "lateral" may not require any particular orientation. Both walls may be considered lateral. The inner porous layer is disposed within these solid peripheral walls and has a superior porous surface 110 and an inferior porous surface 112. A central cavity 118 extends in a superior-inferior direction through spinal implant 100. Central cavity 118 is defined by an inner solid surface 111 and an inner porous surface 114 which form a graft window. The interior surfaces of the graft window also contain a maximized amount of porous material for optimal bone in-growth. As best shown in FIG. 1, the inner walls of central cavity 118 are substantially defined by inner porous surface 114. The large inner porous surface area provides substantial internal surfaces for bony ingrowth into spinal implant 100. Inner porous surface 114 is interspersed with internal solid surface 111 to enhance cavity rigidity and to improve manufacturability and manufacturing quality. Central cavity 118 extends along the length and height of spinal implant 100 and allows for autogenous and/or allogenic bone graft material, being comprised of cancellous and/or corticocancellous bone graft for example, to be implanted therein. A series of serrations 116 extend across the solid peripheral walls and the inner porous surface in a medial-lateral direction for bidirectional fixation and to maximize surface area for endplate contact with the cage. As more fully described below, the serrations are configured to engage and grip vertebral endplates to prevent or mitigate migration of implanted spinal implant 100. The serrations may be composed of multiple materials and may include a solid tip, a solid root and a porous section. The spacing of the serrations is designed to allow for maximization of porous material on the inferior and superior surfaces to support fusion.

Figure 4:
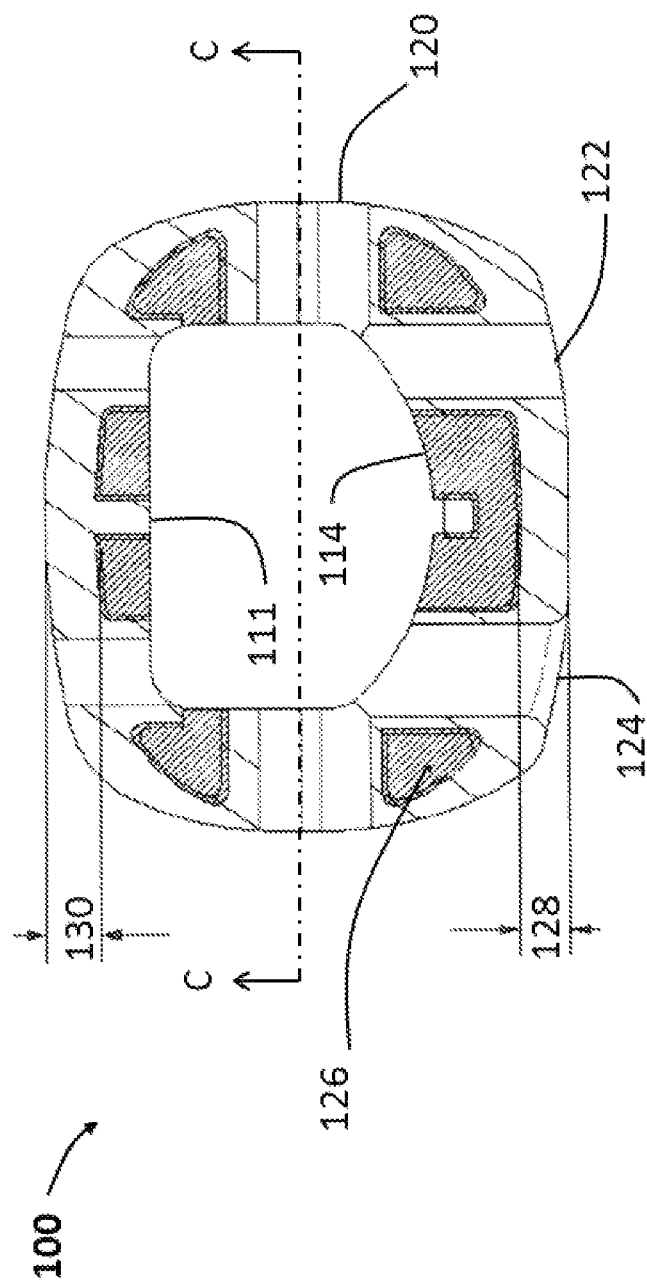
FIG. 4 is top cross-sectional view along line A-A of the spinal implant of FIG. 2.
Figure 5:
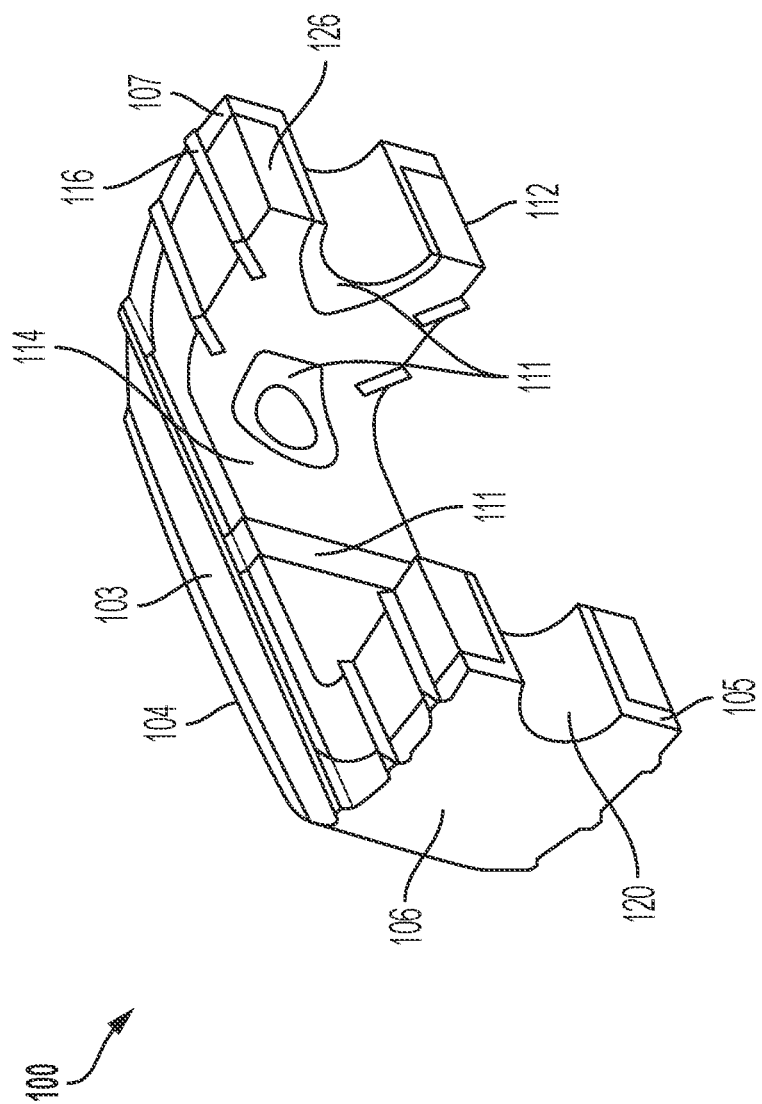
FIG. 5 is a perspective cross-sectional view along line B-B of the spinal implant of FIG. 3.

As best shown in FIGS. 3-5, a medial and a lateral wall thickness 105 and 107 vary along an anterior-posterior direction. Wall thickness as described in this disclosure is denoted by a surface thickness transverse to the specific wall, for example, surface thickness 105 of medial wall indicates wall thickness. Spinal implant 100 is configured to have maximum solid peripheral wall thickness at the anterior and posterior ends for enhanced strength. The central wall areas are thinner allowing for increased porous layer thickness and graft window area to promote bony ingrowth into spinal implant 100. In a preferred embodiment, and only by way of example, an anterior solid wall thickness 128 may be 0.0465" and a posterior wall thickness 130 may be 0.0495" to optimize spinal implant 100 strength and potential for bone ingrowth vis-à-vis porous layers and the graft window. In another embodiment, an anterior solid wall thickness 128 may be 0.465" and a posterior wall thickness 130 may be 0.495". Ranges of wall thicknesses for the anterior and posterior walls can be from about 0.01 to 0.80 inches, though other values are contemplated. The lateral and medial wall thicknesses are at least 0.25 mm, and can be 0.5 mm, 0.75 mm, and 1.0 mm in other embodiments. Ranges of wall thicknesses for the lateral and medial walls can be from about 0.1 to 2 mm, though other values are contemplated. The solid peripheral walls are configured to provide a smooth exterior surface to the spinal implant, which reduces tissue damage and reduces insertion force during implantation. In other embodiments, material may be machined from any of the surfaces to create a smooth surface finish, which may further prevent tissue damage during implantation. This is especially true in connection with implants formed by 3D printing methods or additive manufacturing processes, which often result in even solid portions having a rougher surface finish. In other embodiments, the inner porous surface may be solid for added structural integrity. Further, other embodiments may include vertical solid I-shaped portions within the cavity for added compressive strength.

A lateral window 120 extends across medial solid wall 106 and lateral solid wall 108. Lateral window 120 reduces the stiffness of implant 100 and also allows for visualization through the lateral aspect of the implant under fluoroscopy imaging. The lateral window may be tapered or configured in any other shape to achieve these functions. A first hole 122 and a second threaded hole 124 are present on anterior solid wall 102 and posterior solid wall 104. In other embodiments, either or both holes may be threaded or unthreaded. First hole 122 is an anti-rotation slot facilitating precise insertion of the spinal implant. First hole 122 may also be a second lateral window to reduce the stiffness of implant 100 and also allow visualization through the anterior aspect of the implant under fluoroscopy imaging Second threaded holed 124 is configured to engage with an insertion tool (not shown) to implant spinal implant 100. As best shown in FIG. 5, lateral window 120, first hole 122 and second threaded hole 124 are defined by the solid peripheral wall with the solid layer extending into the inner side of the holes, i.e., toward the central cavity, to enhance rigidity at these holes. Spinal implant 100 includes a nose 109 as best shown in FIG. 6. Nose 109 includes first hole 122 and second threaded hole 124 and is generally wedge-shaped with a smooth exterior surface to aid in the insertion of the spinal implant into the intervertebral space, including, in certain instances, causing distraction of the vertebral bodies.

FIG. 7 shows a detailed view of serrations 116. Serrations 116 have a triangular cross-sectional area. Other cross-sectional areas are contemplated, such as square, trapezoidal, similar shapes having one or more curved walls, and the like. The apex of the triangular cross-section area extends away from spinal implant 100 to engage with vertebral endplates. The serrations are solid and can be integral to the solid peripheral walls to form a solid monolithic frame. In some embodiments, the composition of a serration 116 can vary, such that it may have a solid apex and a porous base. Serration height above superior and inferior porous surfaces 110, 112, and an angle A1 with respect to these surfaces are configured to ensure that serrations firmly contact vertebral endplates to prevent or mitigate spinal implant 100 migration from the intervertebral space. In a preferred embodiment, and only by way of example, angle A1 may be 110 degrees with a serration height of 0.014". In other embodiments, for example, angle A1 may be 130-140 degrees with the opposing surface of serration 116 being perpendicular to superior or inferior porous surface 110, 112, as the case may be (in other words, an interior angle from the apex of serration 116 of 40-50 degrees), with the height of serration being 0.014" to 0.030"; wall thicknesses can be 0.25 mm to 0.5 mm. Serrations 116 have solid roots 132 extending into inner porous layer 115 for enhanced rigidity and manufacturability. Solid wall thickness around the lateral windows provide additional rigidity to protect the porous material from damage. The porous sections are maximized for optimal surface area on the inferior and superior surfaces of the implants, leading to more area for bone in-growth. The proportion of porous to solid material in all areas is designed to maintain a minimal level of strength for device performance. Feature 103 is designed to improve the manufacturing quality of the device, as well as protect the porous material in that area during insertion into the vertebral space. The distribution of external solid wall thickness is designed to provide strength in axes of known loading in spine implants. Superior and inferior porous surfaces 110, 112 can be angled with respect to one another to create a lordotic implant, such that the height of anterior solid wall 102 is greater than the height of posterior solid wall 104. The angle between superior and inferior porous surfaces 110, 112 can be about 4 degrees, and in other embodiments, at various values within the range of 0.5 to 10 degrees.

Figure 8:
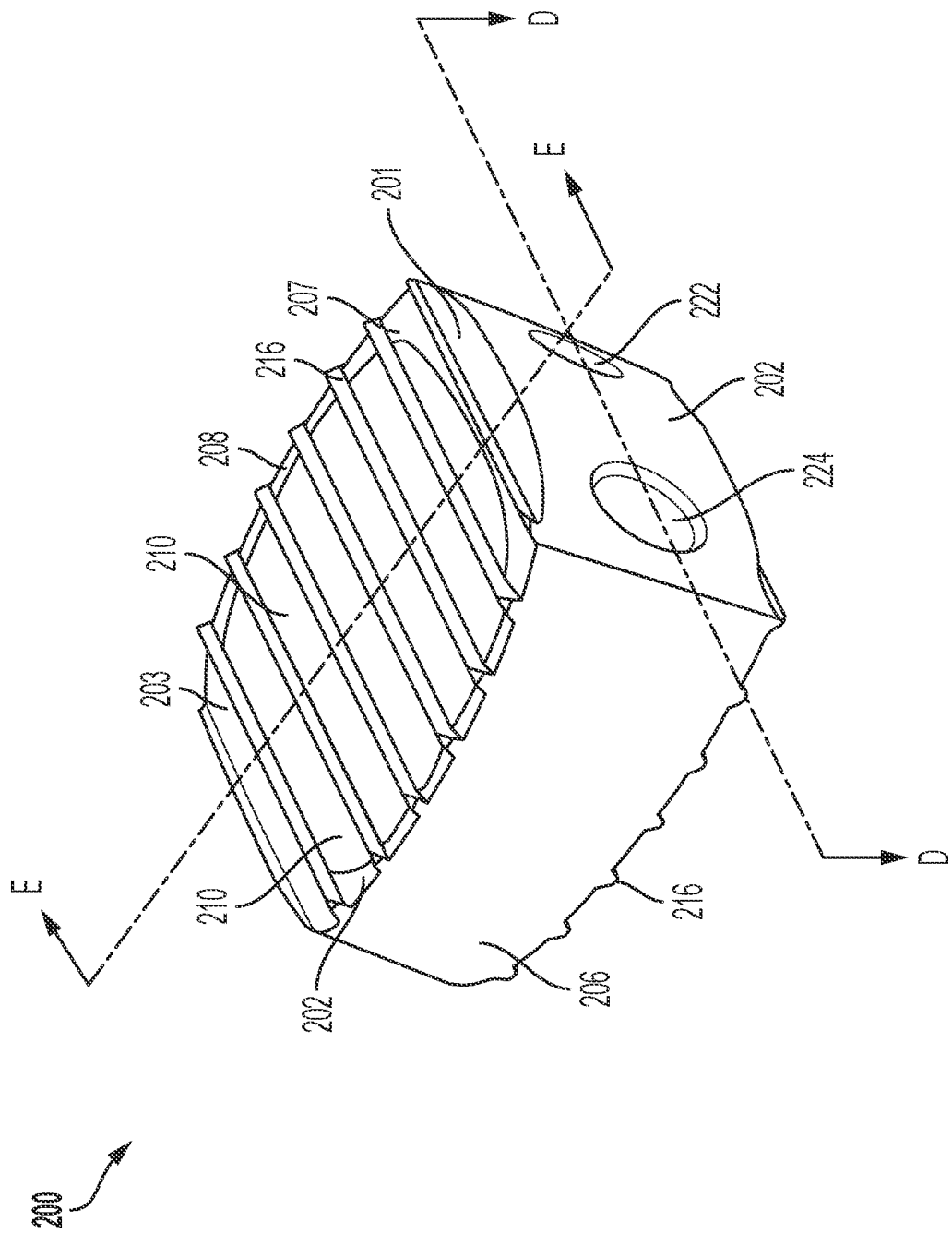
FIG. 8 is front perspective view of a spinal implant according to another embodiment of the present invention.

Referring now to FIGS. 8-10, there is shown a spinal implant 200 according to another embodiment of the present invention. Spinal implant 200 is similar to spinal implant 100, and therefore like elements are referred to with similar numerals within the 200-series of numbers. For instance, spinal implant 200 includes anterior solid wall 202, posterior solid wall 204, medial solid wall 206 and lateral solid wall 208 that are interconnected and form an integral wall. However, spinal implant 200 does not have a central cavity. Instead, the entire internal region bounded by the solid peripheral walls contains porous material. Consequently, spinal implant 200 provides greater surface area and volume for bone ingrowth without the need for bone graft material or the like. Solid serrations 216 span across the entire medial-lateral length in this embodiment and further enhance rigidity of spinal implant 200. The greater number of serrations 216 present in spinal implant 200 also increases vertebral endplate contact and securement. Spinal implant 200 also includes first hole 224 and second threaded hole 222. As best shown in a top cross-sectional view of spinal implant (FIG. 9), first hole 224 and second threaded hole 222 extend only from anterior solid wall 202 to inner porous layer 215. Blind holes 222 and 224 in this embodiment allow for additional porous layer within spinal implant 200. Furthermore, posterior wall 204 is a solid continuous wall with no holes and therefore strengthens spinal implant 200. Similarly, as shown in FIGS. 8 and 10, spinal implant 200 does not have a lateral window on medial solid wall 206 and lateral solid wall 208. Therefore, solid material is maximized on medial solid wall 206 and lateral solid wall 208 to enhance the strength of this construct. The size and location of lateral window(s) can vary. The solid portions may extend from the superior surface to the inferior surface for added structural rigidity.

Figure 11:
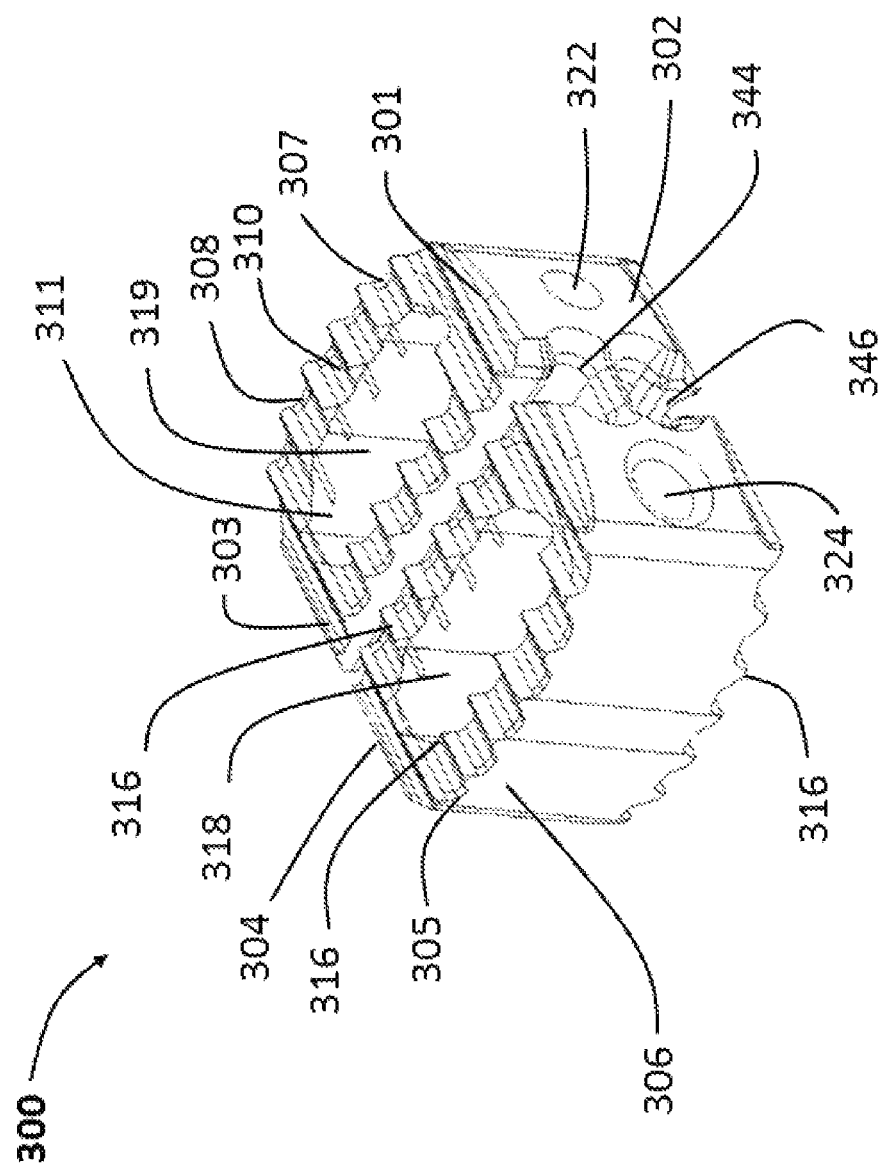
FIG. 11 is front perspective view of a spinal implant according to another embodiment of the present invention.

FIGS. 11-16 show a spinal implant 300 according to another embodiment of the present invention. Spinal implant 300 is similar to spinal implant 100, and therefore like elements are referred to with similar numerals within the 300-series of numbers. For instance, spinal implant 300 includes anterior solid wall 302, posterior solid wall 304, medial solid wall 306 and lateral solid wall 308 that are interconnected and form an integral wall. Spinal implant 300 includes a first cavity 318 and a second cavity 319 separated by anchor channels 344 and 346 to receive anchors as disclosed in U.S. Pat. Nos. 8,349,015; 9,138,275; 9,138,276 and 9,788,968, the disclosures of which are hereby incorporated by reference herein as if fully set forth herein. Cavities 318 and 319 are defined by inner solid surface 311 and inner porous surface 314 forming graft windows. As best shown in FIG. 11, the inner walls of cavities 318 and 319 are substantially defined by inner porous surface 314. The large inner porous surface 314 provide substantial internal surfaces for bony ingrowth into both cavities of spinal implant 300. Inner porous surface 314 is interspersed with internal solid surface 311 to enhance cavity rigidity. The cavities extend along the length of spinal implant 300 and allow for bone graft material to be implanted therein.

Figure 14:
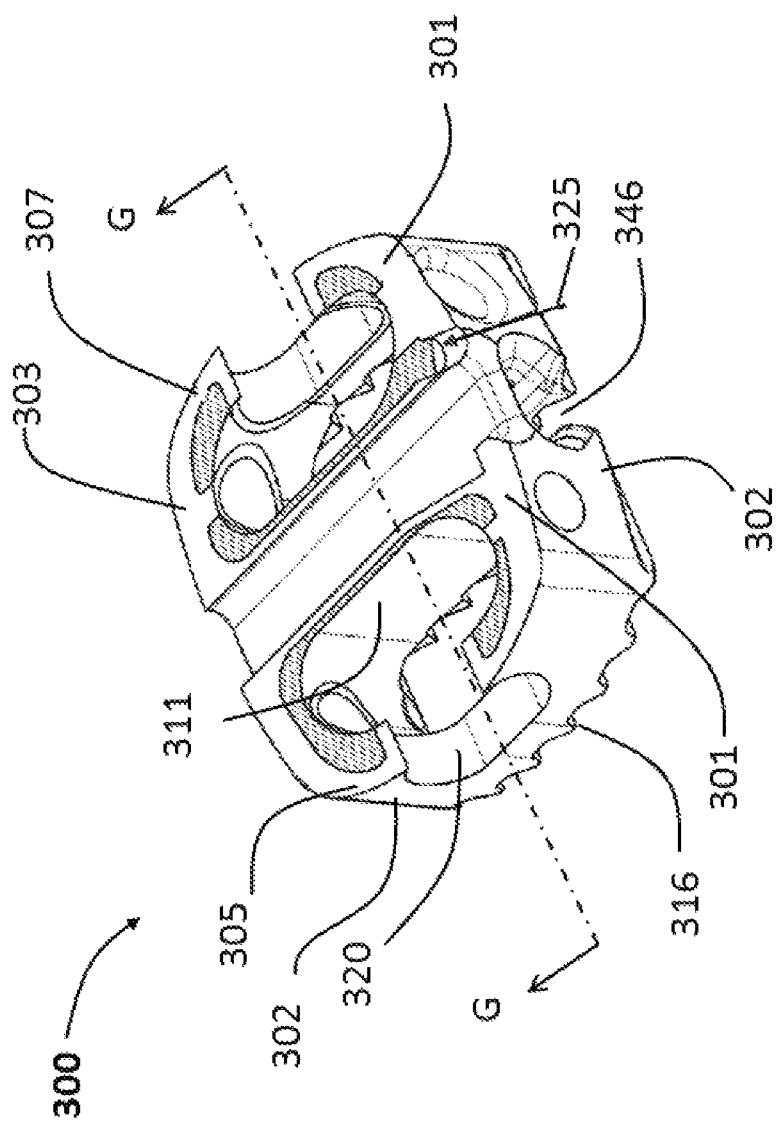
FIG. 14 is a perspective cross-sectional view along line F-F of the spinal implant of FIG. 13.
Figures 15, 16:
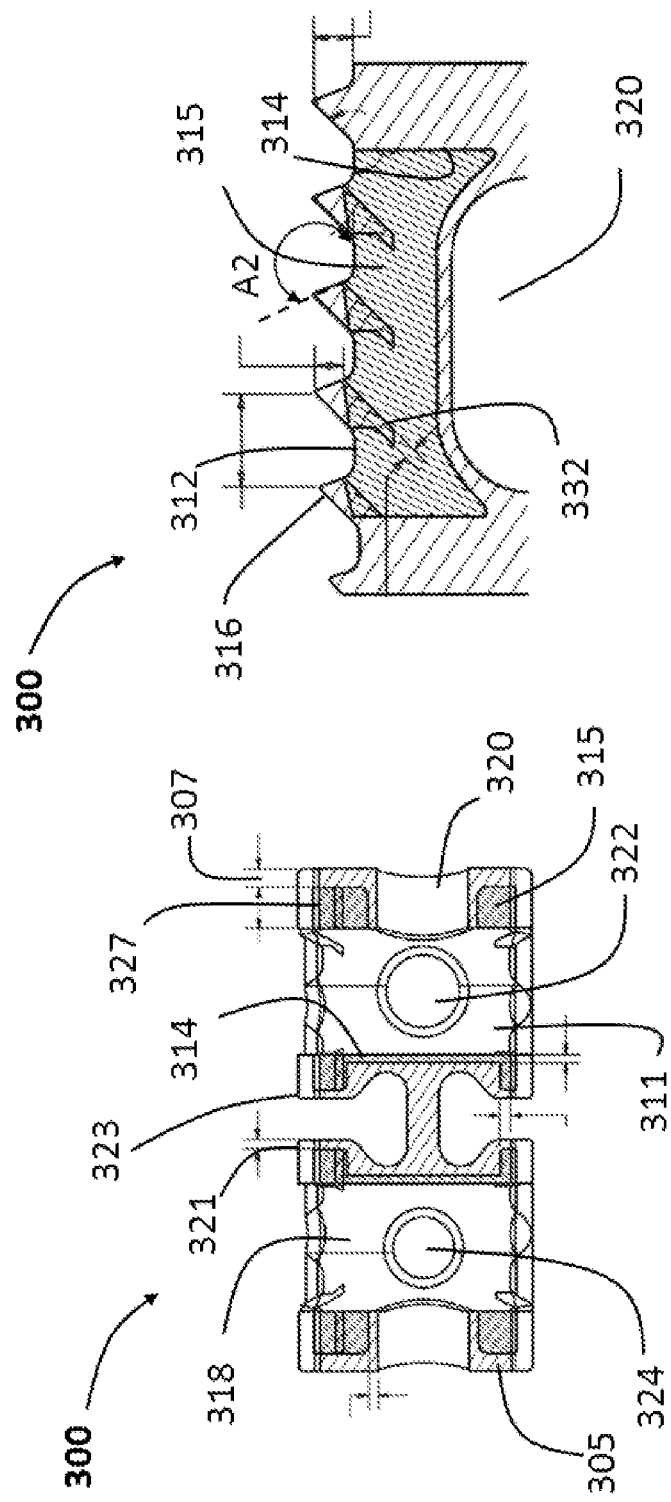
FIG. 15 is a front cross-sectional view along line G-G of the spinal implant of FIG. 14.
FIG. 16 is a cross-sectional detailed view of the spinal implant of FIG. 11.

FIGS. 14 and 15 show the varying solid peripheral wall thickness and porous layer thickness of spinal implant 300. Medial and lateral wall thickness 305 and 307 vary along an anterior-posterior direction and are configured to have maximum solid peripheral wall thickness at the anterior and posterior ends for enhanced strength. The central wall areas are thinner allowing for increased porous layer thickness and graft window area to promote bony ingrowth into spinal implant 300. Inner medial and lateral wall thickness 321 and 323 are less than the outer medial wall thickness 305, 307 as best shown in FIG. 15. In a preferred embodiment, and only by way of example, a lateral solid wall thickness 307 may be 0.020" and a lateral porous wall thickness 327 may be 0.046" to optimize spinal implant 300 strengthen and potential for bone ingrowth vis-à-vis porous layers and graft windows. In another embodiment, a lateral solid wall thickness 307 may be 0.20" and a lateral porous wall thickness 327 may be 0.46". Ranges of wall thicknesses for the lateral solid wall thickness 307 can be from about 0.01 to 0.80 inches, though other values are contemplated. Ranges of wall thicknesses for the lateral porous wall thickness 327 can be from about 0.01 to 1.0 inches, though other values are contemplated.

Details of serration 316 are shown in FIG. 16. Serrations 316 have a triangular cross-sectional area. The apex of the triangular cross-section area extends away from spinal implant 300 to engage with vertebral endplates. The serrations are solid and can be integral to the solid peripheral walls to form a solid monolithic frame. Serration height above superior and inferior porous surfaces 310, 312, and an angle A2 are configured to ensure that serrations firmly contact vertebral endplates to prevent or mitigate spinal implant 300 migration from the intervertebral space. In a preferred embodiment, and only by way of example, angle A2 may be 110 degrees with serration height of 0.025". Serration 316 has solid roots 332 extending into inner porous layer 315 for enhanced rigidity and manufacturability.

Figure 17:
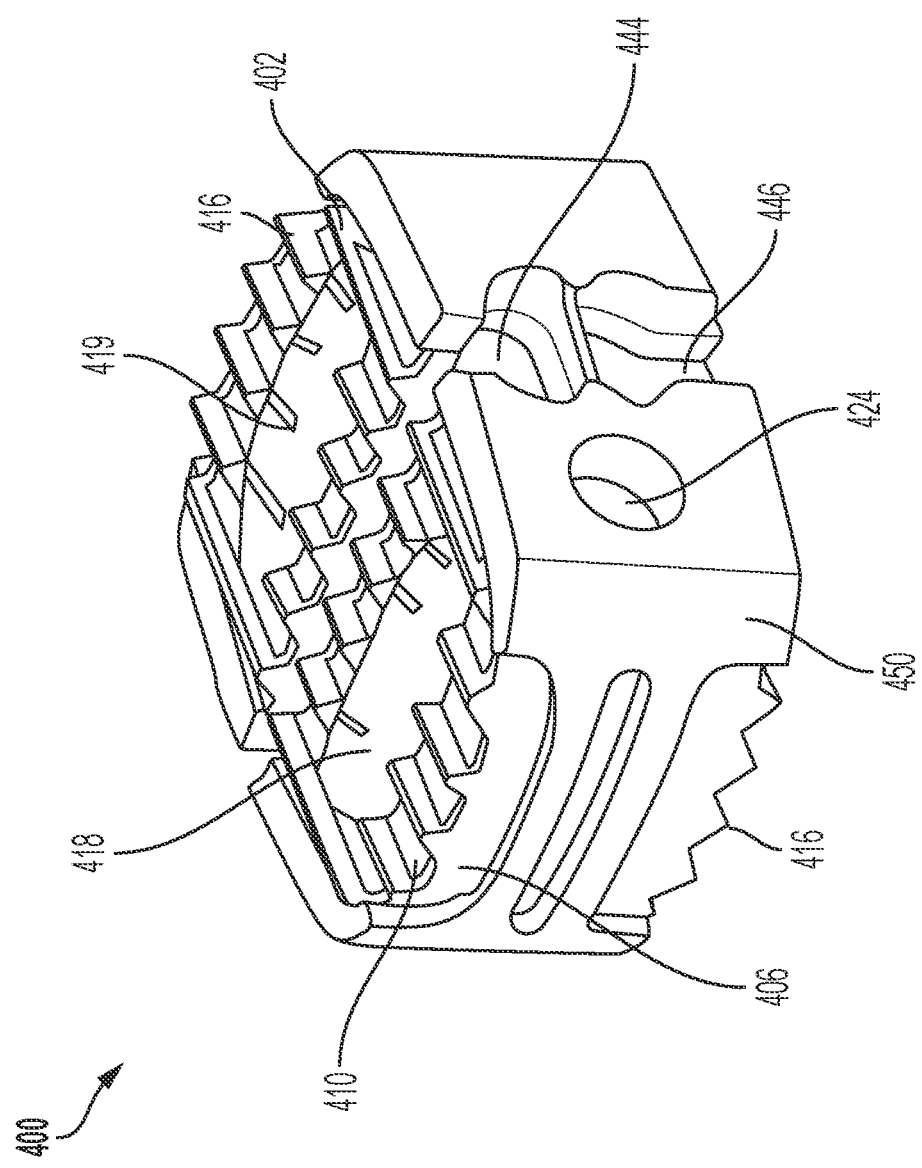
FIG. 17 is a front perspective view of a spinal implant according to another embodiment of the present invention.
Figure 19:
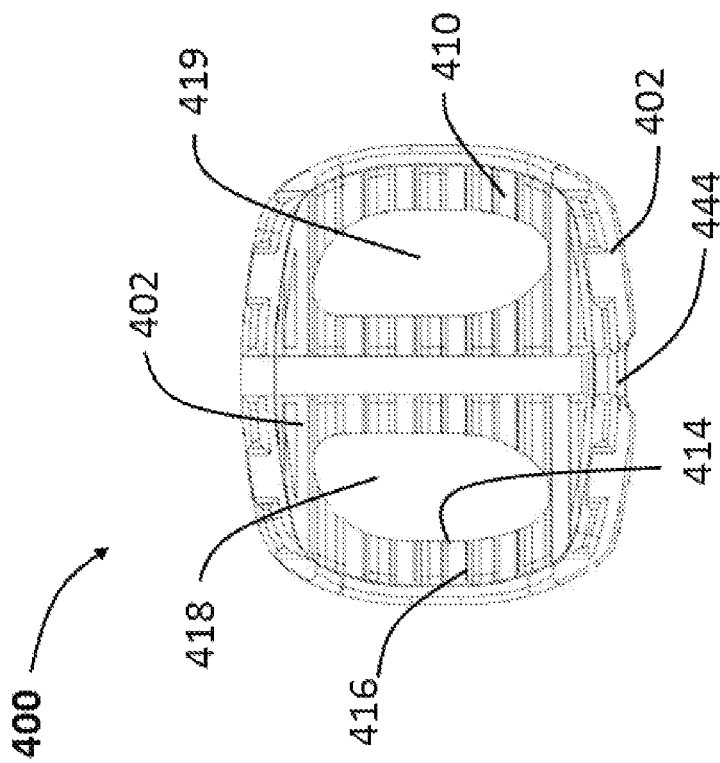
FIG. 19 is a top view of a spacer portion of the spinal implant of FIG. 17.
Figure 18:
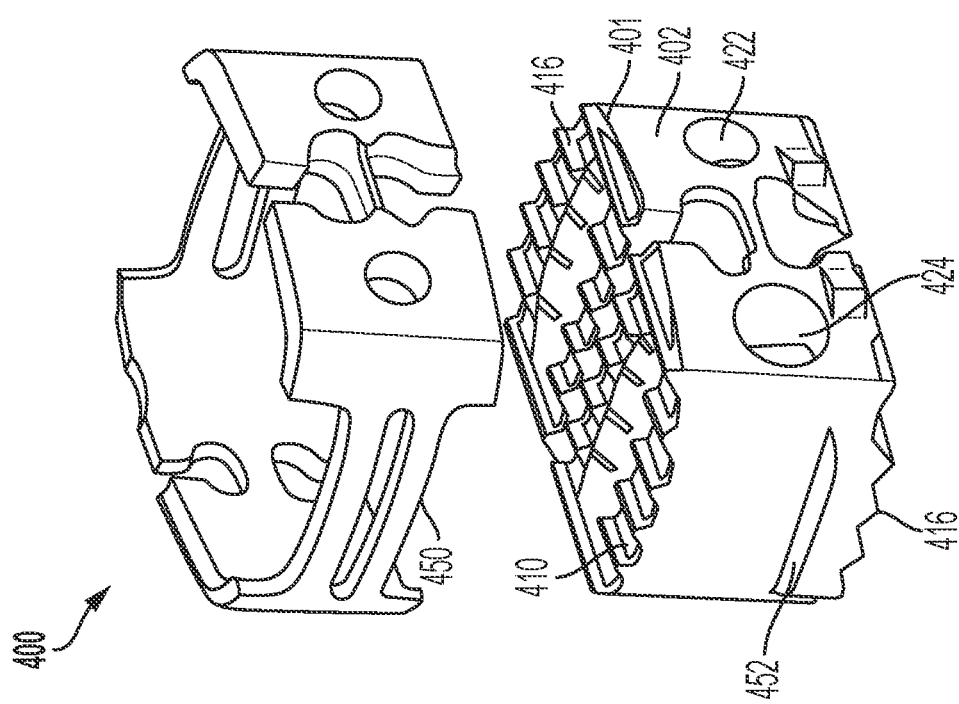
FIG. 18 is an exploded perspective view of the spinal implant of the FIG. 17.
Figure 20:
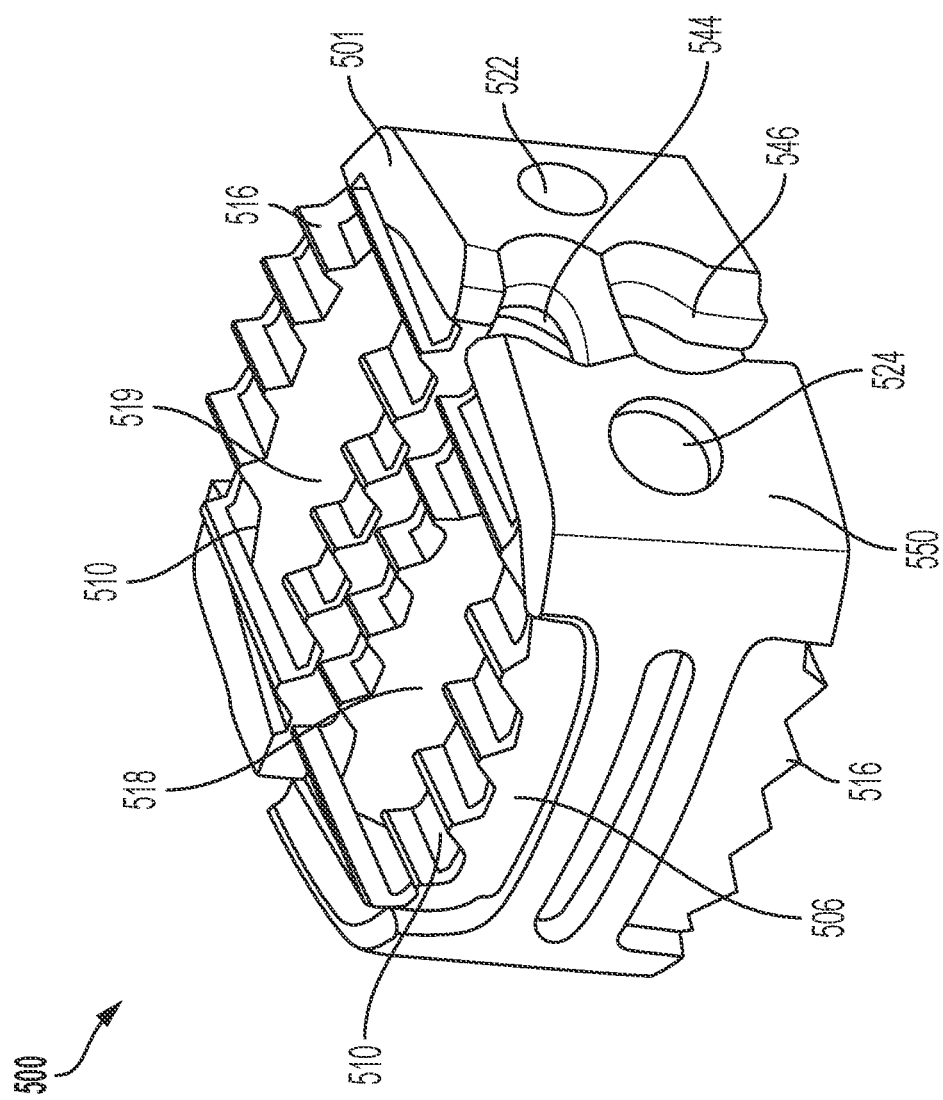
FIG. 20 is a front perspective view of a spinal implant according to another embodiment of the present invention.
Figure 21:
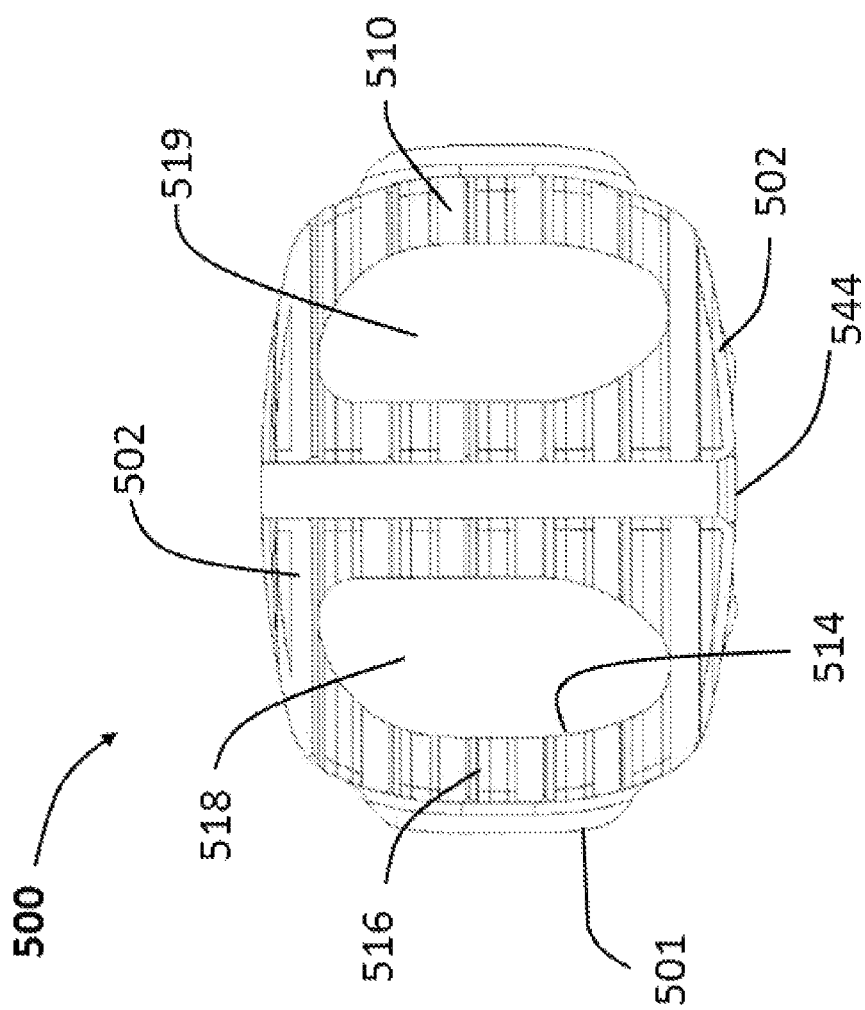
FIG. 21 is a top view of the spinal implant of FIG. 20.
Figure 22:
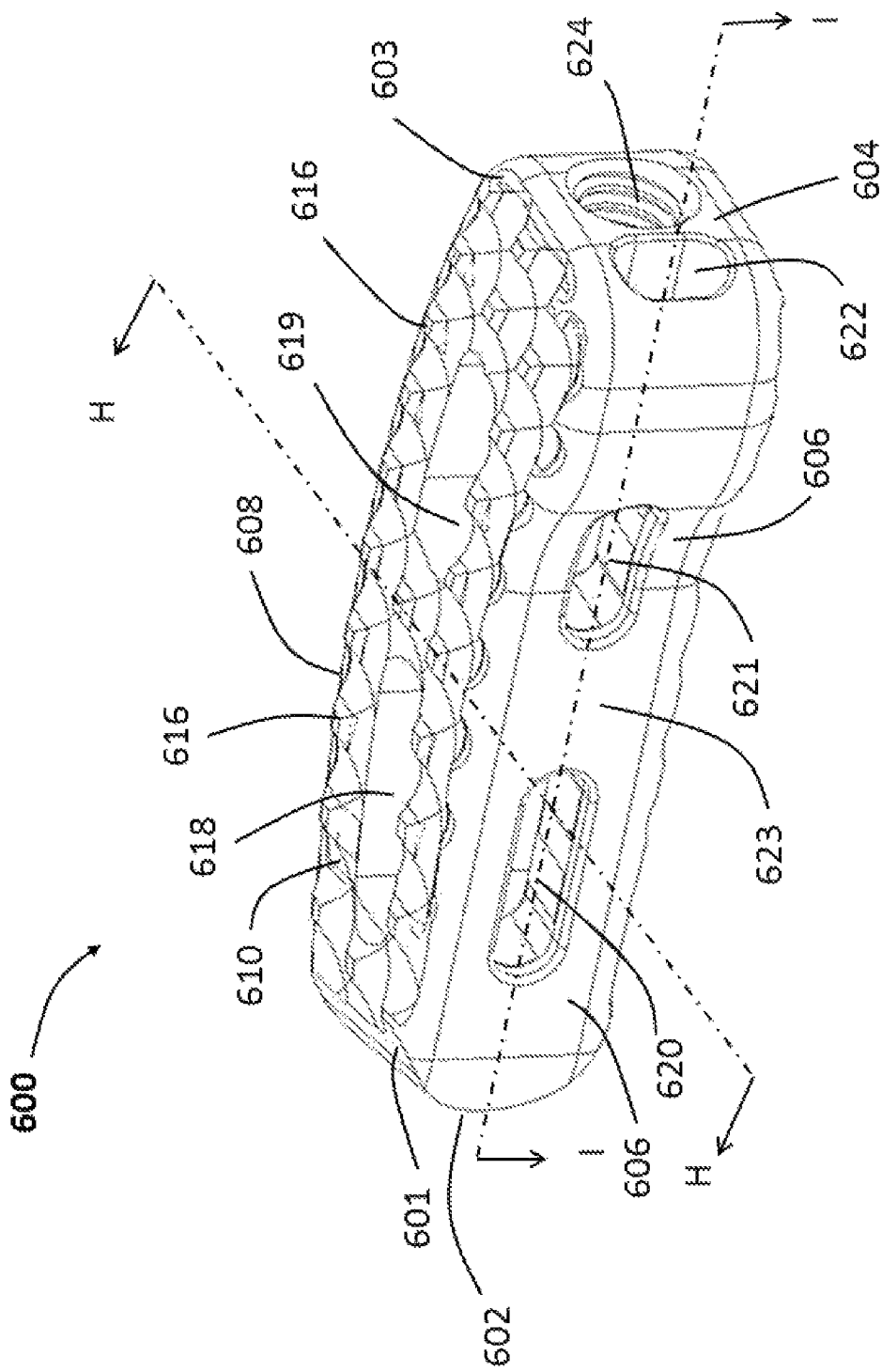
FIG. 22 is a front perspective view of a spinal implant according to another embodiment of the present invention.

Referring now to FIGS. 17-19, there is shown a spinal implant 400 according to another embodiment of the present invention. FIGS. 20 and 21 show a spinal implant 500 according to yet another embodiment of the present invention. Spinal implants 400 and 500 are similar to spinal implant 300, and therefore like elements are referred to with similar numerals within the 400-series and 500-series of numbers respectively. For instance, spinal implant 400 includes first cavity 418 and second cavity 419 separated by anchor channels 444 and 446. Similarly, spinal implant 500 includes first cavity 518 and second cavity 519 separated by anchor channels 544 and 546. However, spinal implant 400 includes a jacket 450 that can be attached to the solid peripheral walls. Spinal implant 500 has an integrated jacket 550. Jacket 450 and 550 allow for visualization through the lateral aspect of the implants under fluoroscopy imaging and can show the overall height of the implant relative to the vertebral endplates. Jackets can be made of titanium or other suitable metals or polymers to increase overall implant strength.

Figure 23:
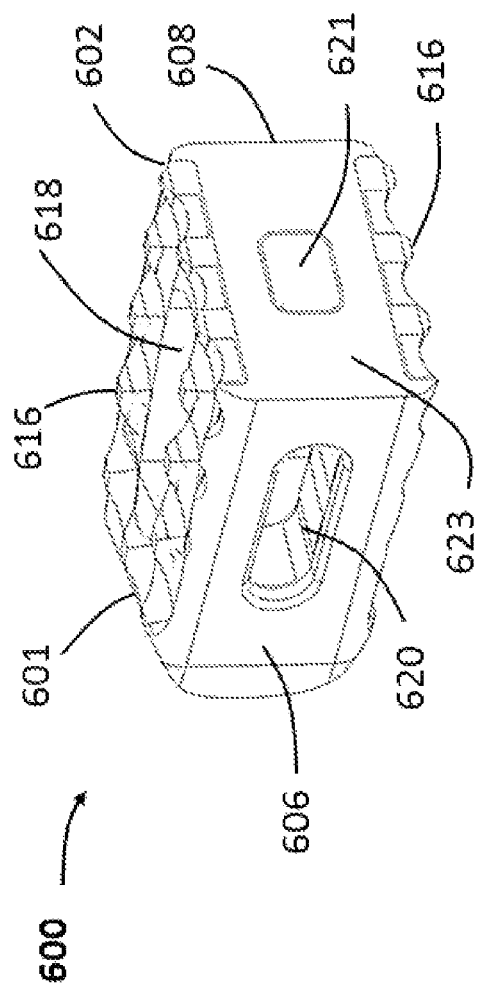
FIG. 23 is perspective cross-sectional view along line H-H of the spinal implant of FIG. 22.
Figure 24:
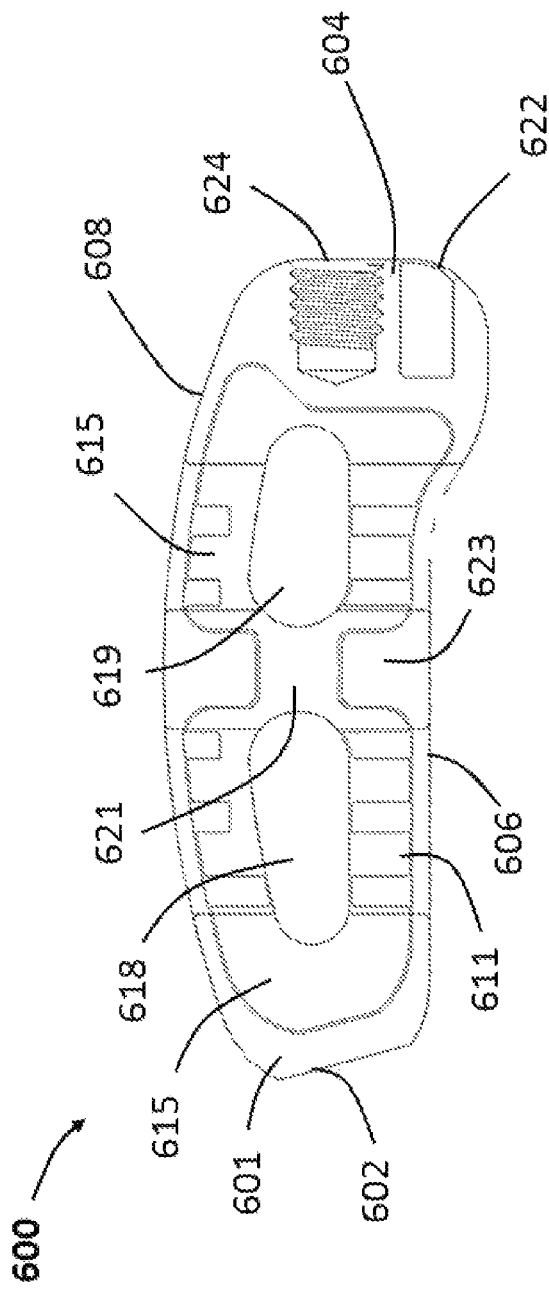
FIG. 24 is a top cross-sectional view along line I-I of the spinal implant of FIG. 22.
Figure 25:
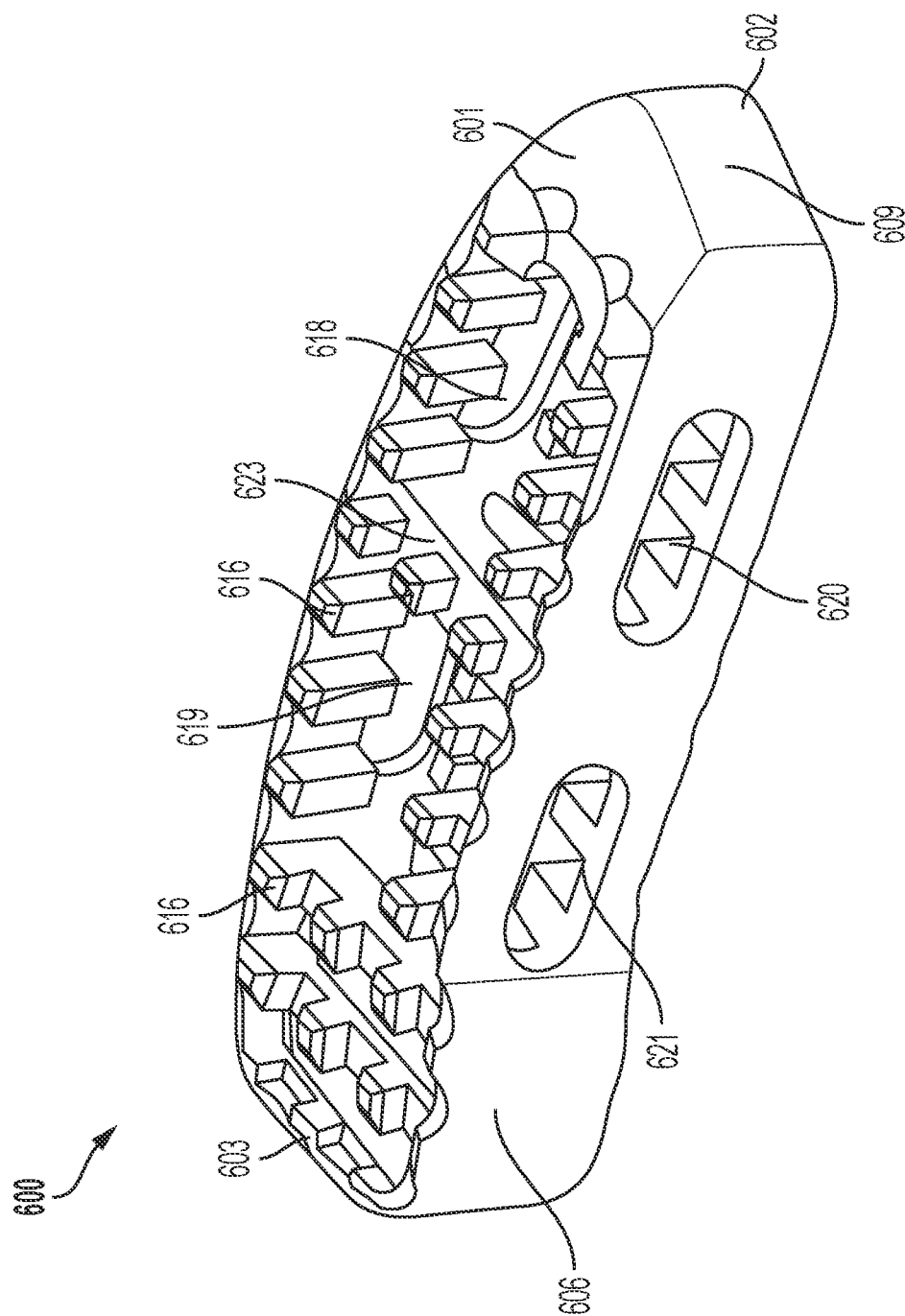
FIG. 25 is a front perspective view of a solid body of the spinal implant of FIG. 22.

FIGS. 22-25 show a spinal implant 600 according to another embodiment of the present invention. Spinal implant 600 is suitable for implantation from a posterior approach. Spinal implant 600 is similar to spinal implant 100, and therefore like elements are referred to with similar numerals within the 600-series of numbers. For instance, spinal implant 600 includes anterior solid wall 602, posterior solid wall 604, medial solid wall 606 and lateral solid wall 608. However, spinal implant 600 has two cavities 616 and 619 separated by a crossbar 623. Each cavity has a lateral window 620, 621 on medial solid wall 606 and lateral solid wall 608. As spinal implant 600 is configured for implantation from a posterior approach, second threaded hole 624 to engage with an insertion tool (not shown) is located on posterior solid wall 604. An anti-rotation slot 622 is also located on the posterior solid wall to aid implantation of spinal implant 600. A window 621 through crossbar 623 links first cavity 618 and second cavity 619 as best shown in FIG. 23. Window 621 is covered with porous inner layer to facilitate bone growth across the first and second cavity. As best seen in FIG. 25, spinal implant 600 has teeth 616 instead of the serrations discussed in the previous embodiments. Teeth 616 are generally integrated to the solid peripheral walls to add strength to the spinal implant construct. Teeth 616 are also integrated along crossbar 623 and provide additional support for teeth located away from the side walls. Nose 609 shown in FIG. 25 is generally wedge-shaped with a smooth exterior surface to distract vertebral bodies during insertion of the spinal implant into the intervertebral space. In a preferred embodiment, and only by way of example, solid wall thickness at the nose may be 1.5 mm, lateral solid wall and medial solid wall thickness may be 0.75 mm to optimize spinal implant 600 strengthen and potential for bone ingrowth vis-à-vis inner porous layer and graft windows.

Figure 26B:
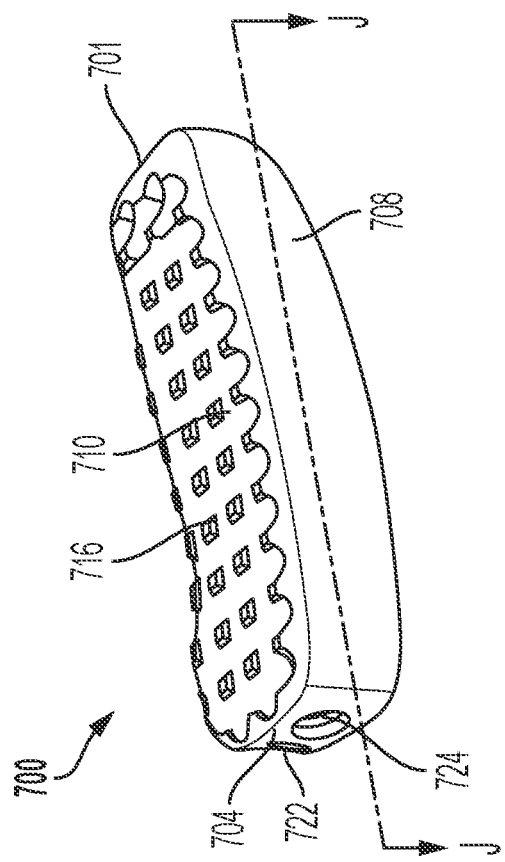
FIG. 26B is a back perspective view of the spinal implant of FIG. 26A.
Figure 26A:
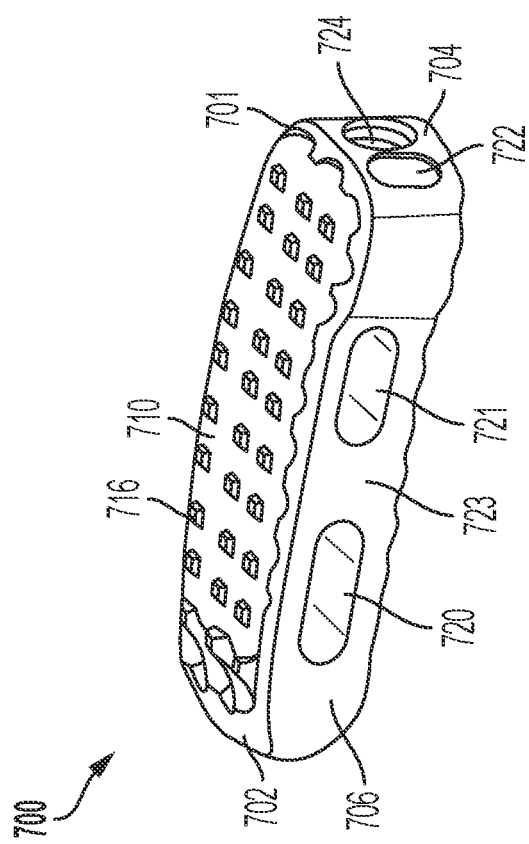
FIG. 26A is a front perspective view of a spinal implant according to another embodiment of the present invention.
Figure 27:
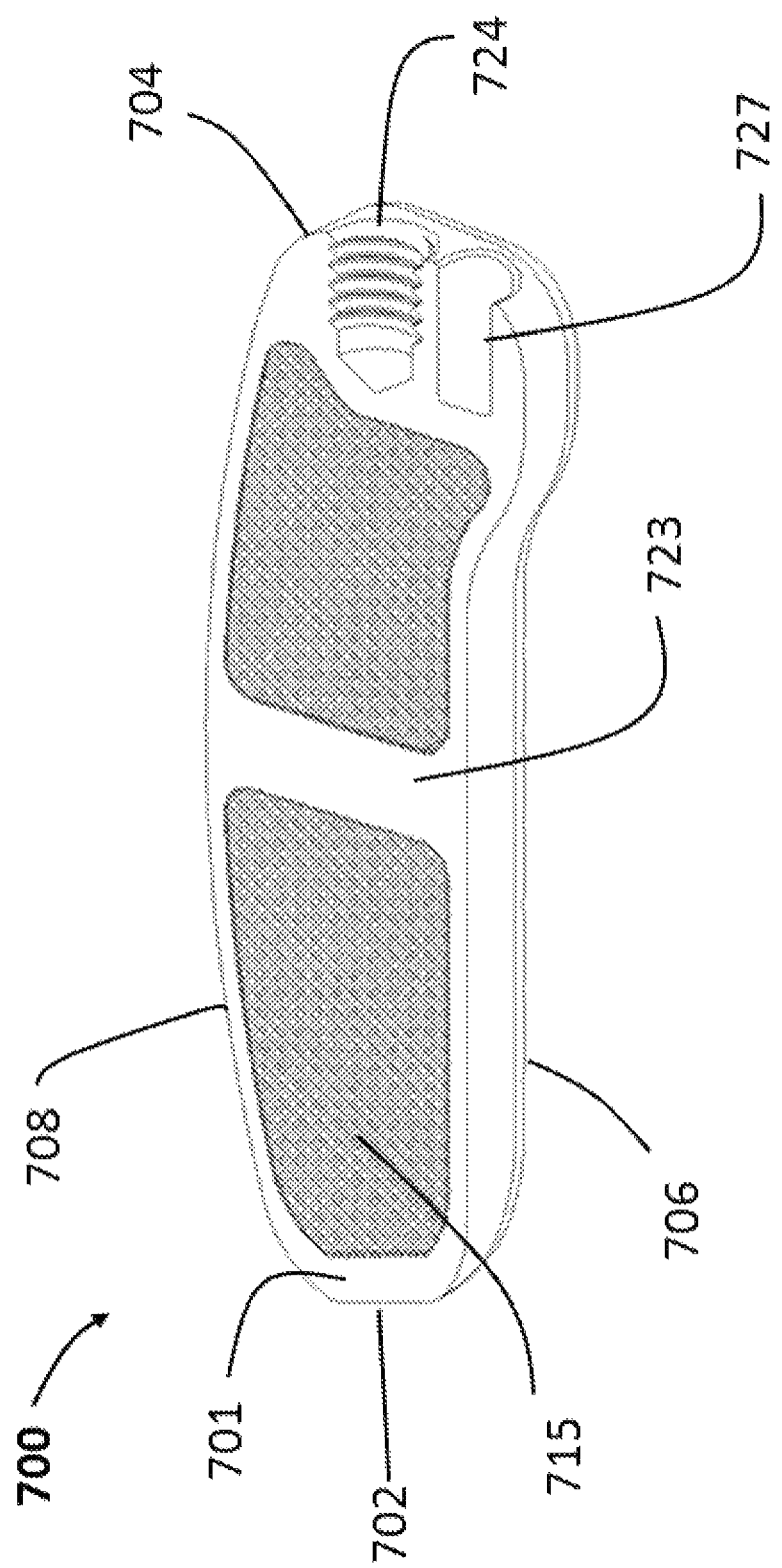
FIG. 27 is a top cross-sectional view along line J-J of the spinal implant of FIG. 26B.

Referring now to FIGS. 26A-27, there is shown a spinal implant 700 according to another embodiment of the present invention. Spinal implant 700 is similar to spinal implant 600, and therefore like elements are referred to with similar numerals within the 700-series of numbers. For instance, spinal implant 700 includes anterior solid wall 702, posterior solid wall 704, medial solid wall 706 and lateral solid wall 708. However, spinal 700 does not have central cavities. Instead, the entire internal region bounded by the solid peripheral walls contains porous material. Consequently, spinal implant 700 provides a greater surface area and volume for bone ingrowth. Crossbar 723 is also completely solid without any openings as best seen in FIG. 27.

Figure 28:
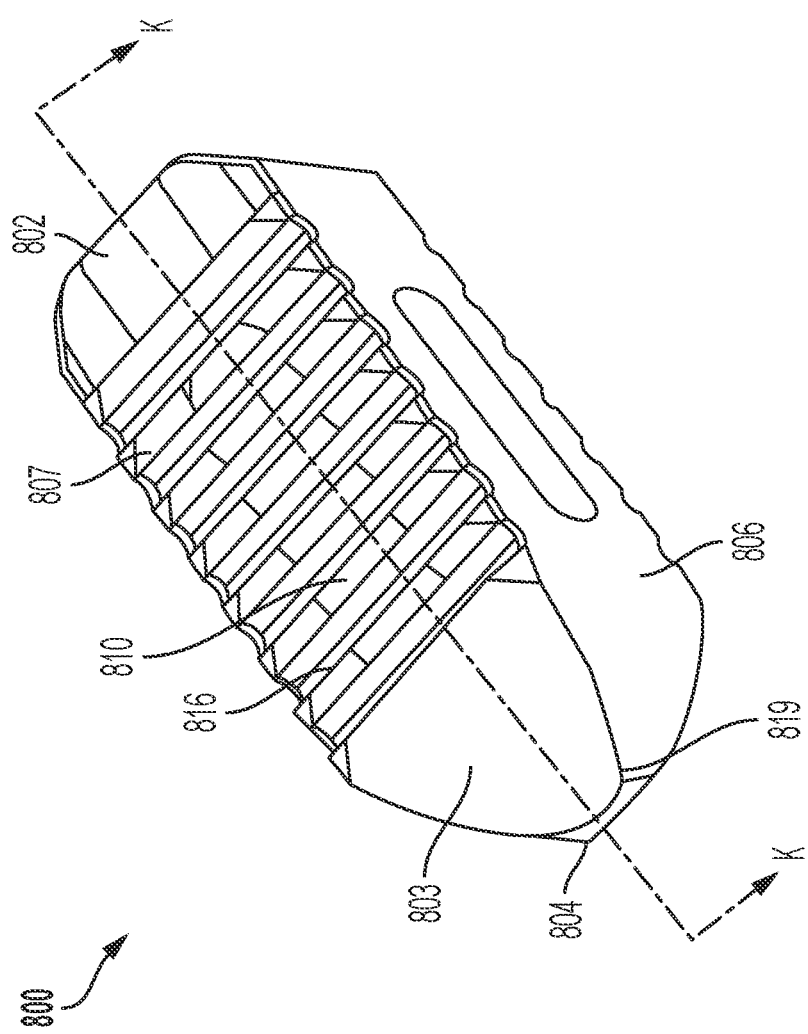
FIG. 28 is a top perspective view of a spinal implant according to another embodiment of the present invention.
Figure 29:
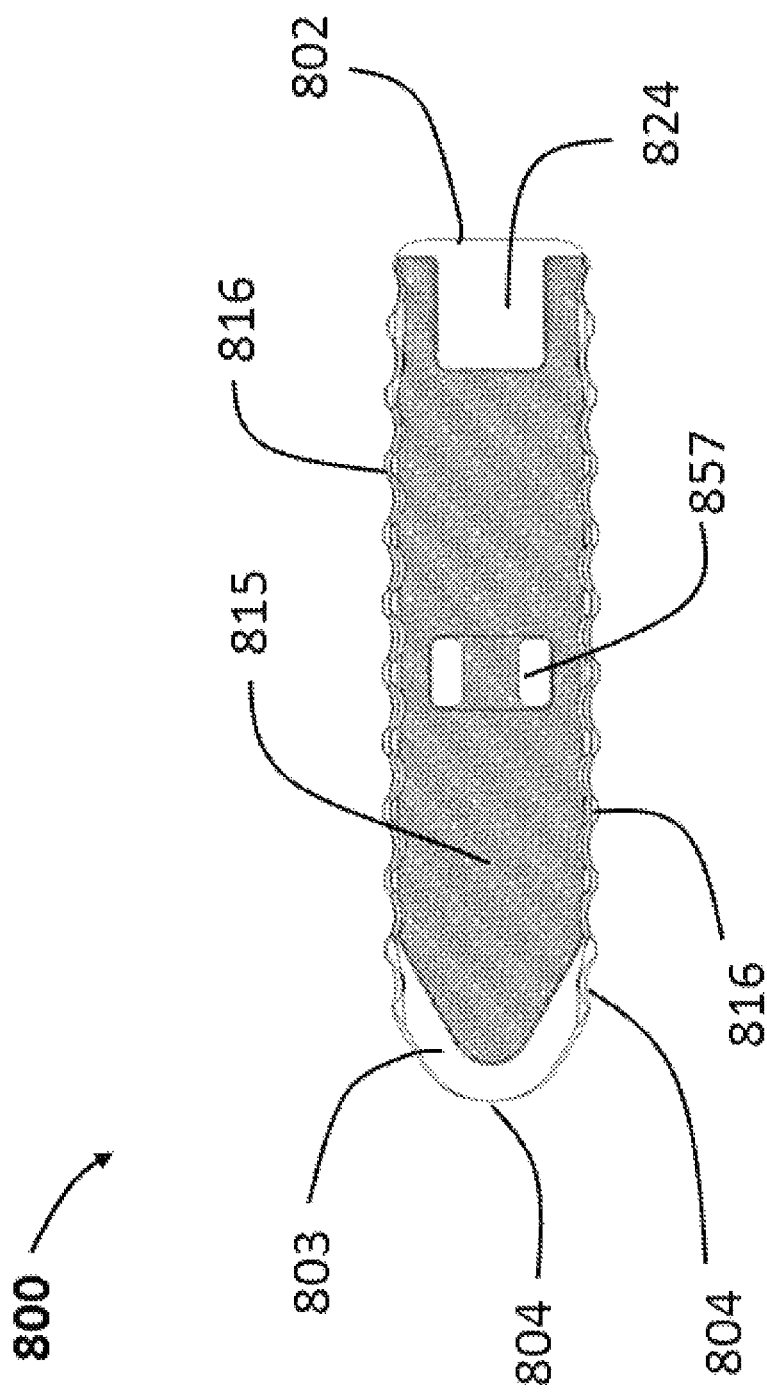
FIG. 29 is a side cross-sectional view along line K-K of the spinal implant of FIG. 28.

FIGS. 28 and 29 show a spinal implant 800 according to another embodiment of the present invention. Spinal implant 800 is similar to spinal implant 200, and therefore like elements are referred to with similar numerals within the 800-series of numbers. For instance, spinal implant 800 includes anterior solid wall 802, posterior solid wall 804, medial solid wall 806 and lateral solid wall 808. Spinal implant 800 includes a wedge-shaped nose 819 to facilitate implant insertion. A solid crossbar 857 extending medial-laterally across porous layer 815 provides rigidity to the construct as best shown in FIG. 29. Radiopaque markers may be provided for visualization of the implant under fluoroscopy imaging.

Figure 31:
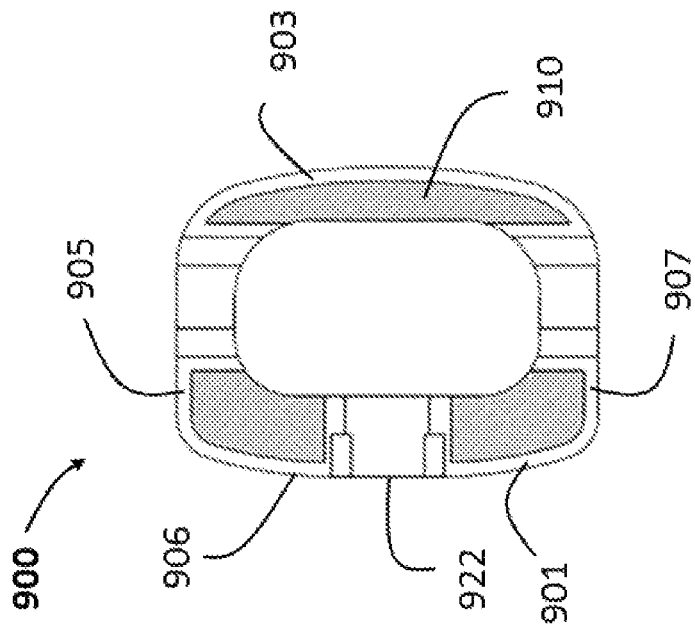
FIG. 31 is top cross-sectional view along line L-L of the spinal implant of FIG. 30.
Figure 30:
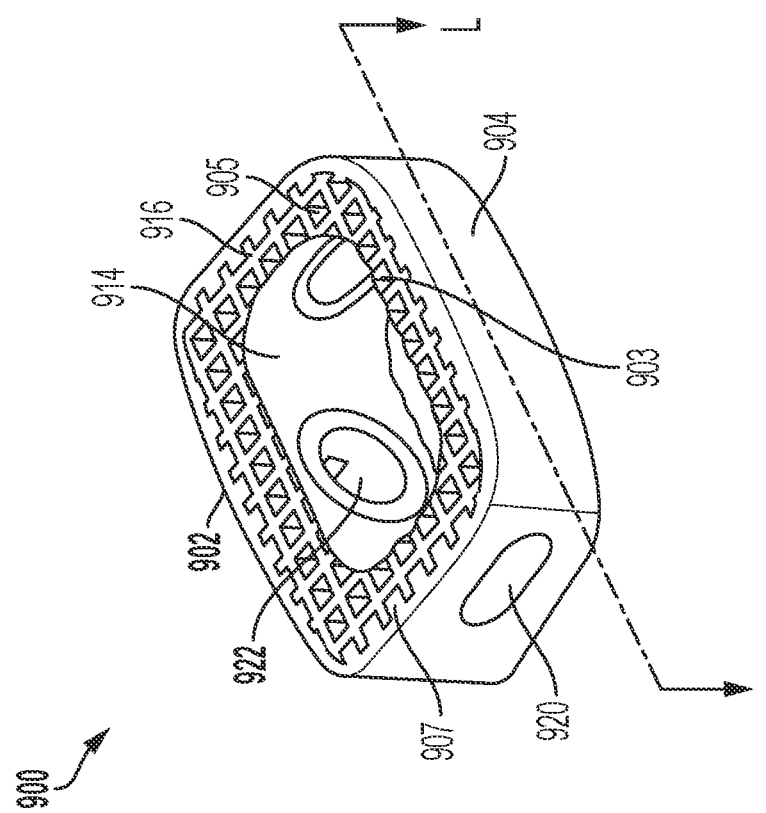
FIG. 30 is a top perspective view of a spinal implant according to another embodiment of the present invention.
Figure 33:
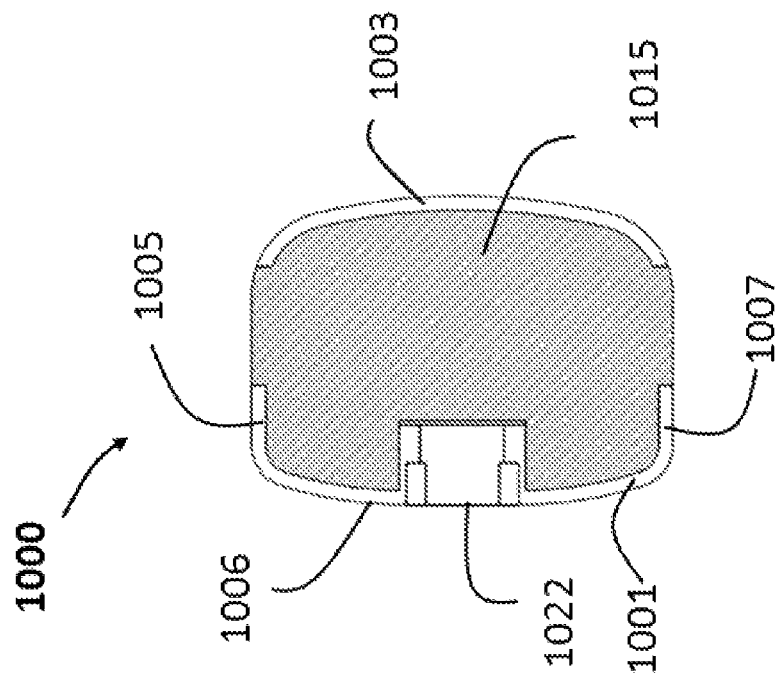
FIG. 33 is top cross-sectional view along line M-M of the spinal implant of FIG. 32.
Figure 32:
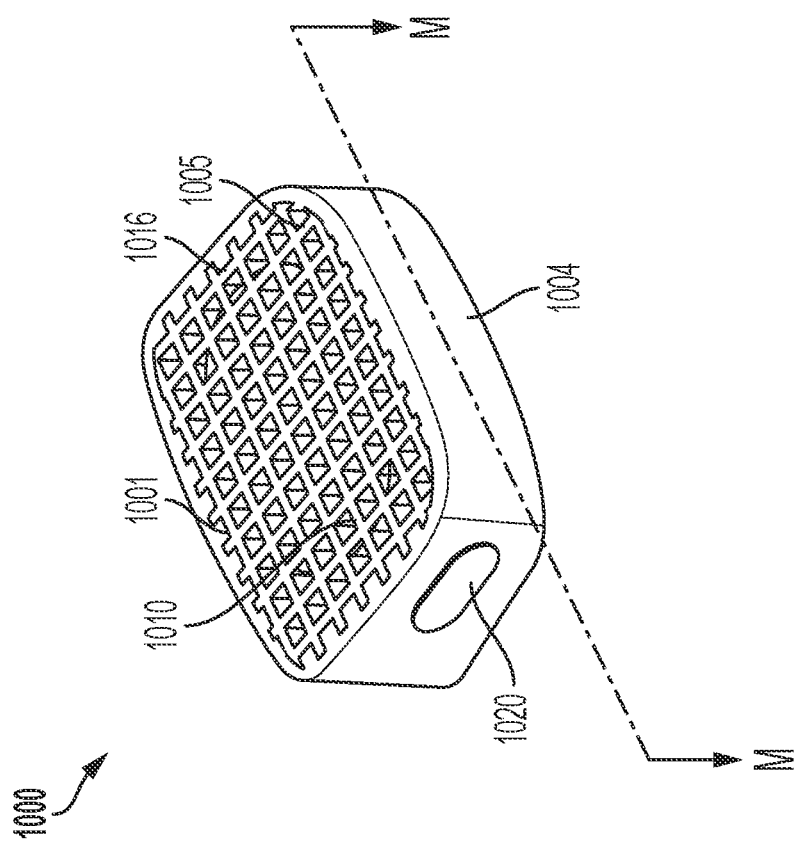
FIG. 32 is a top perspective view of a spinal implant according to another embodiment of the present invention.

Referring now to FIGS. 30 and 31 and FIGS. 31 and 32, there is shown a spinal implant 900 and a spinal implant 1000 respectively according to other embodiments of the present invention. Spinal implant 900 and spinal implant 1000 are similar to spinal implant 100, and therefore like elements are referred to with similar numerals within the 900-series and 1000-series of numbers. For instance, spinal implant 900 includes anterior solid wall 902, posterior solid wall 904, medial solid wall 906 and lateral solid wall 908. However, spinal implant 900 does not have serrations. Instead, spinal implant 900 has ribs 916 extending in the medial-lateral and anterior-posterior direction with greater coverage over inner porous layer. Ribs 916 are teeth that are similar in nature to teeth 616. Ribs 916 serve the same purpose as the serrations of previously described embodiments and as teeth 616 to resist migration of the implant 900 within the intervertebral space, and to have optimal spacing to facilitate bone growth into the superior and inferior surfaces of implant 900. Spinal implant 1000 includes similar ribs 1016 but does not have a central cavity but is instead completely packed with porous material.

Figure 35:
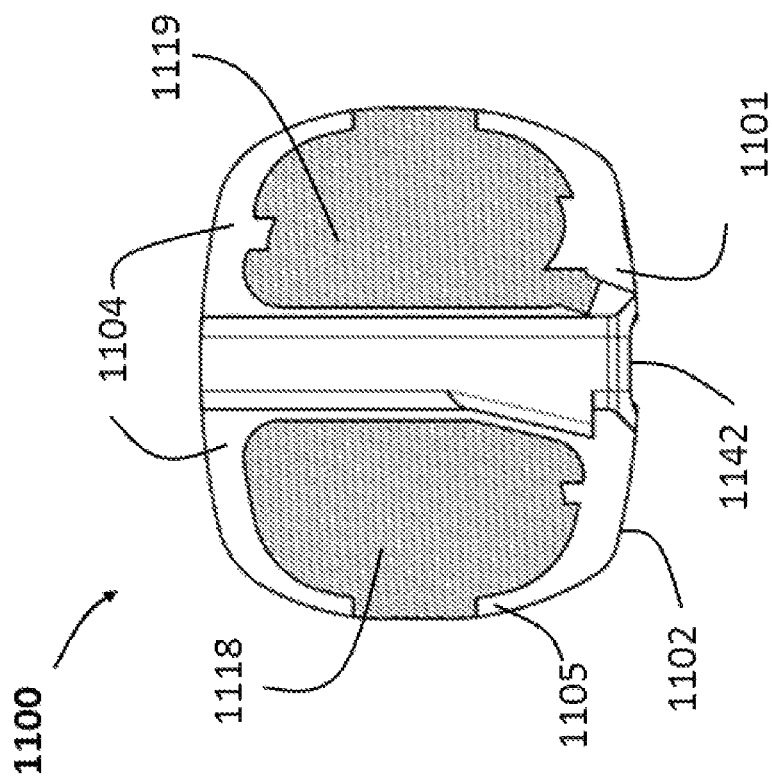
FIG. 35 is a top cross-sectional view along line N-N of the spinal implant of FIG. 34.
Figure 34:
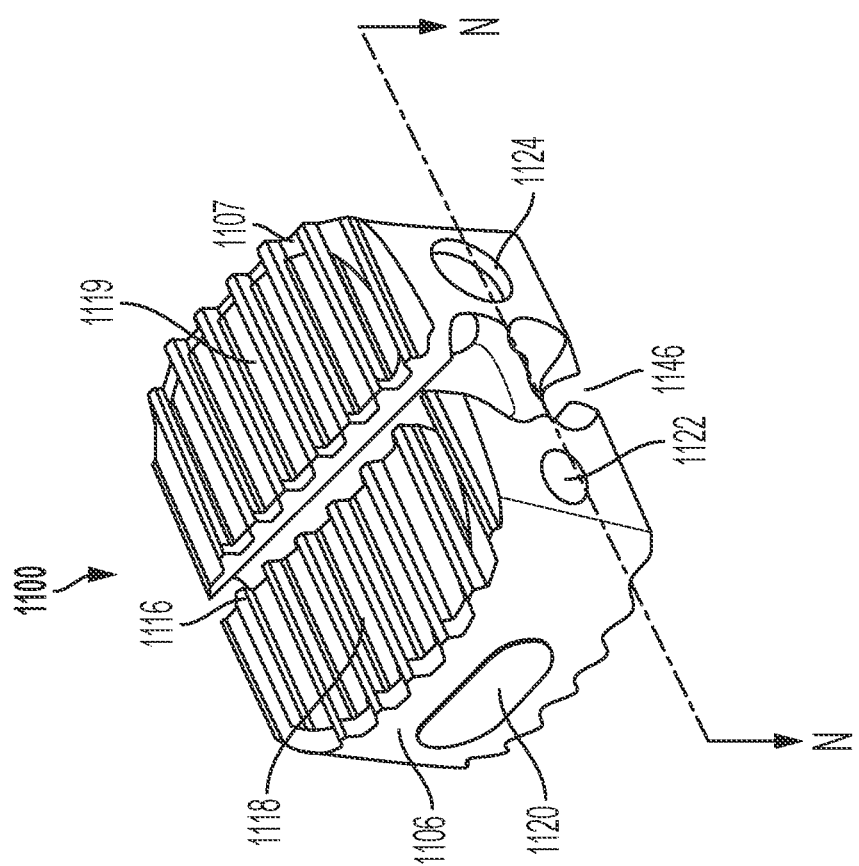
FIG. 34 is a top perspective view of a spinal implant according to another embodiment of the present invention.

FIGS. 34 and 35 show a spinal implant 1100 according to another embodiment of the present invention. Spinal implant 1100 is similar to spinal implant 300, and therefore like elements are referred to with similar numerals within the 800-series of numbers. For instance, spinal implant 1100 includes anterior solid wall 1102, posterior solid wall 1104, medial solid wall 1106 and lateral solid wall 1108. Spinal implant 1100, however, does not include central cavities but is instead completely packed with porous material to have two porous layers 1118 and 1119 separated by channel 1146 as best shown in FIG. 35. Cavities packed with porous material enhance rigidity of spinal implant 1100 and also improve bone-porous material ingrowth.

Figure 40:
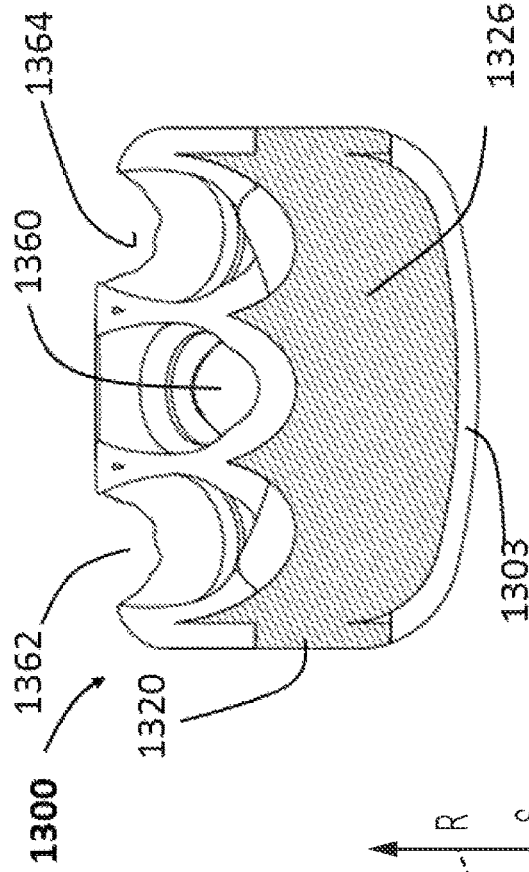
FIG. 40 is a bottom cross-sectional view along line R-R of the spinal implant of FIG. 39.
Figure 41:
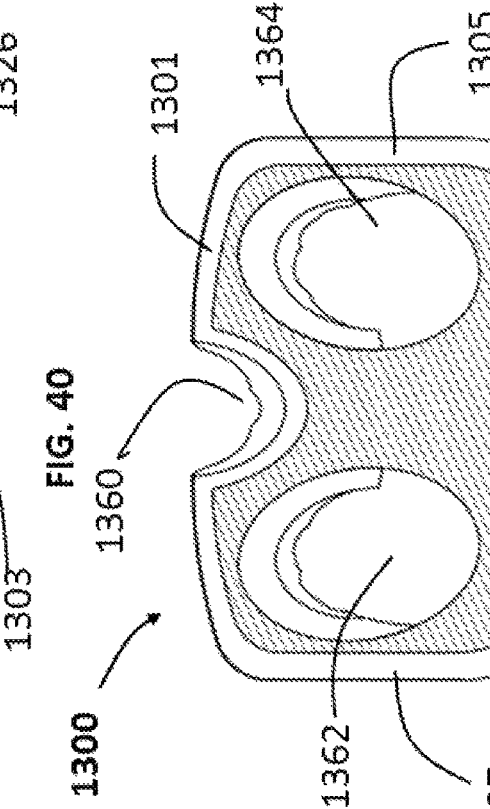
FIG. 41 is a bottom cross-sectional view along line S-S of the spinal implant of FIG. 39.
Figure 39:
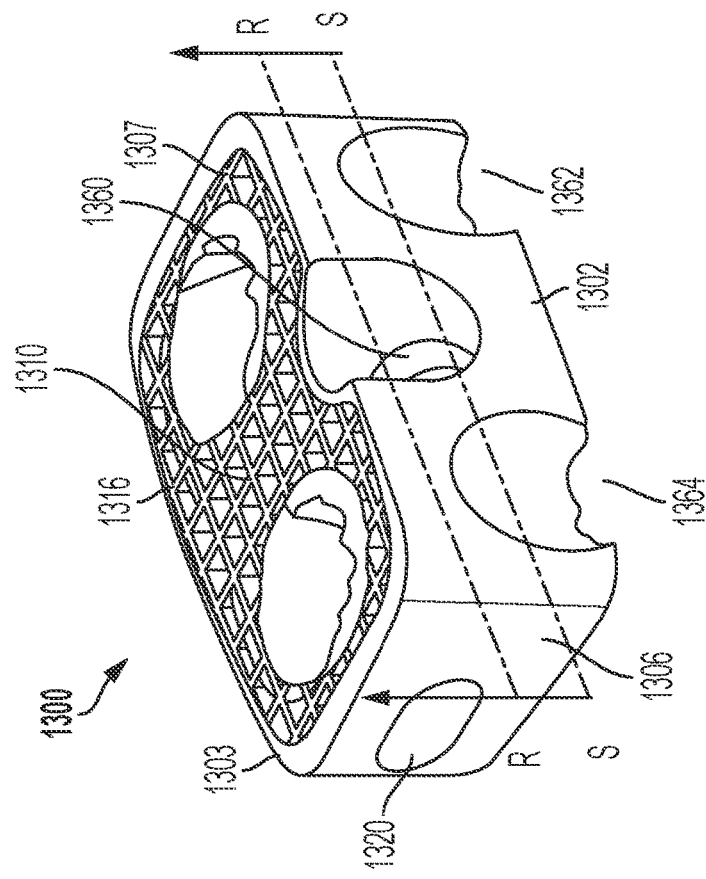
FIG. 39 is a top perspective view of a spinal implant according to another embodiment of the present invention.

Referring now to FIGS. 36-38 and FIGS. 39-41, there is shown a spinal implant 1200 and a spinal implant 1300 respectively according to other embodiments of the present invention. Spinal implant 1200 and spinal implant 1300 are similar to spinal implant 100, and therefore like elements are referred to with similar numerals within the 1200-series and 1300-series of numbers. For instance, spinal implant 1200 includes anterior solid wall 1202, posterior solid wall 1204, medial solid wall 1206 and lateral solid wall 1208. Spinal implants 1200 and 1300 are configured to be implanted in an anterior-posterior direction with the implants having a tapered shape in an anterior-posterior direction as best shown in FIGS. 36 and 39. Spinal implant 1200 includes a bore hole 1260 configured to receive a fastener (not shown)

in a generally superior-inferior direction to secure the implant to a vertebral. Two additional bore holes 1262 and 1264 on either side of bore hole 1260 are configured to receive fasteners (not shown) in an inferior-superior direction as best shown in FIG. 36. Similarly, spinal implant 1300 includes bore holes 1360, 1362 and 1364 to secure fixation of spinal implant 1300 to a vertebral body as best shown in FIG. 39. Instead of serrations shown in spinal implant 100, ribs 1216 and 1316 of spinal implant 1200 and 1300 respectively, extend in a medial-lateral and anterior-posterior direction offering greater coverage over inner porous layers. While spinal implant 1200 has central cavities 1218 and 1219, spinal implant 1300 is completely packed with porous materials as best shown in FIGS. 40 and 41.

The implants described above are each offered in a number of footprints, heights, and lordotic angles to adapt to a variety of patient anatomies.

The implants described above can be manufactured by 3D printing methods or additive manufacturing processes.

The solid and porous portions of the implants described herein are preferably of material suitable for implantation in a patient and capable of providing the necessary strength and durability required for such application. For instance, in certain embodiments, the solid and porous portions are constructed from titanium. However, any other suitable metals or non-metals may be used, and it is contemplated to utilize different materials for the solid and porous portions. The porous surfaces may an average pore diameter between 100-1000 microns with a 30-80% porosity, while a preferred embodiment would have a porosity between 50-70%. The porous surfaces may also have any thickness, for instance between 500-4500 microns, and preferably between 500-1500 microns. This results in a surface that is both strong enough for use in a spinal implant and maximizes bone growth potential. The porous portions of implant 10, as well as the solid portions, can be created through the use of a 3D printing process such as is disclosed in U.S. Pat. Nos. 7,537,664 and 8,147,861; 8,727,387; 8,350,186; 9,135,374; 9,180,010; and U.S. Patent Application Publication No. 2006/0147332, the disclosures of which are hereby incorporated by reference herein. It is also contemplated to form any porous portion via another known or hereafter developed procedure, such as laser etching.

Figure 42:
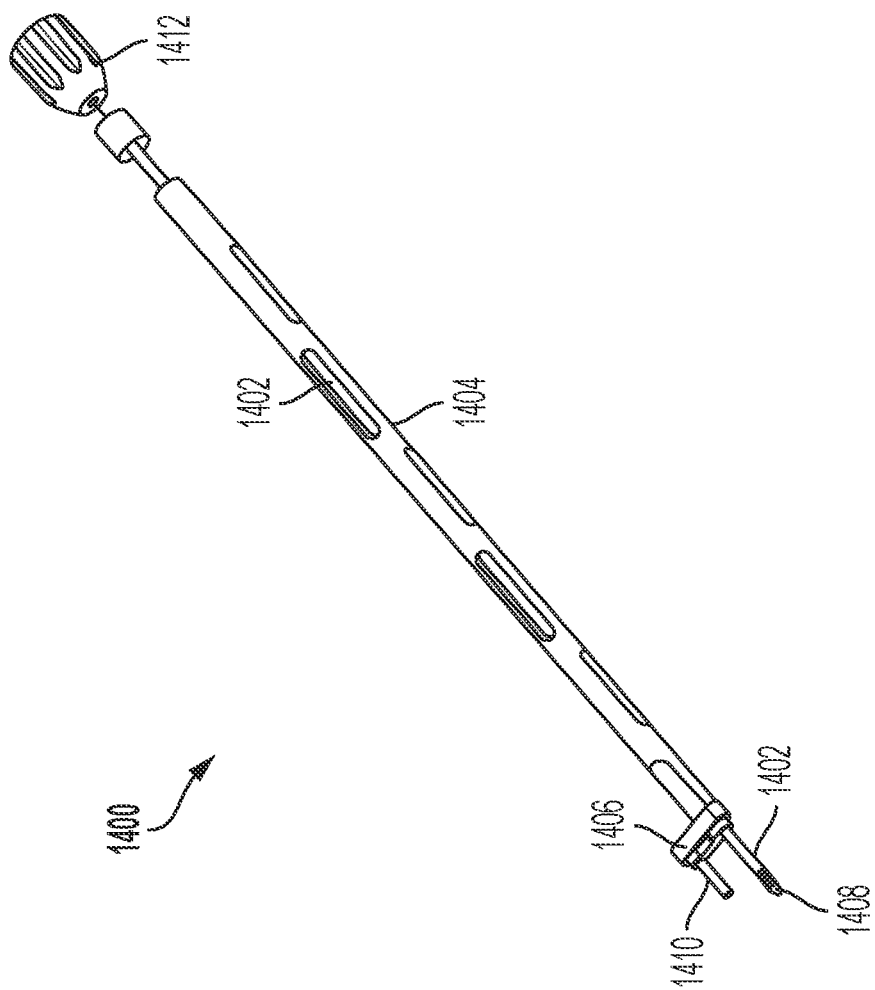
FIG. 42 is a perspective view of an inserter according to an embodiment of the present invention.

FIG. 42 shows a perspective view of a spinal implant inserter 1400 according to another embodiment of the present invention. Inserter 1400 includes a shaft 1402 extending through an outer sleeve 1404. A base 1406 is connected to a distal end of outer sleeve 1404 and includes an aperture to allow shaft 1402 to extend through the base. Base 1406 includes an alignment post 1410 extending distally and parallel to shaft 1402. A proximal end of shaft 1402 is connected to a knob 1412 which includes grooves to allow an operator to conveniently grip and rotate knob 1412. Windows located along outer sleeve 1404 provide visual indication of shaft 1402 rotation when knob 1412 is manipulated by an operator. A distal end of the shaft 1402 includes a threaded tip 1408 sized to engage with a threaded hole in a spinal implant. Similarly, alignment post 1410 is sized to engage with a through hole in the spinal implant to serve as an alignment guide by preventing rotation of the spinal implant when alignment post 1410 and threaded tip 1408 are engaged with the spinal implant. Threaded tip 1408 can be engaged and disengaged from the spinal implant by rotating knob 1402. While inserter 1400 has a threaded tip to engage with spinal implant 100 in this embodiment, other embodiments can have a snap-fit, ball-detent, friction fit or other mechanism at the distal end of the inserter to engage and disengage with a spinal implant. The alignment post can be a spring-loaded retractable element to allow for easy engagement and disengagement from the spinal implant.

Figure 43:
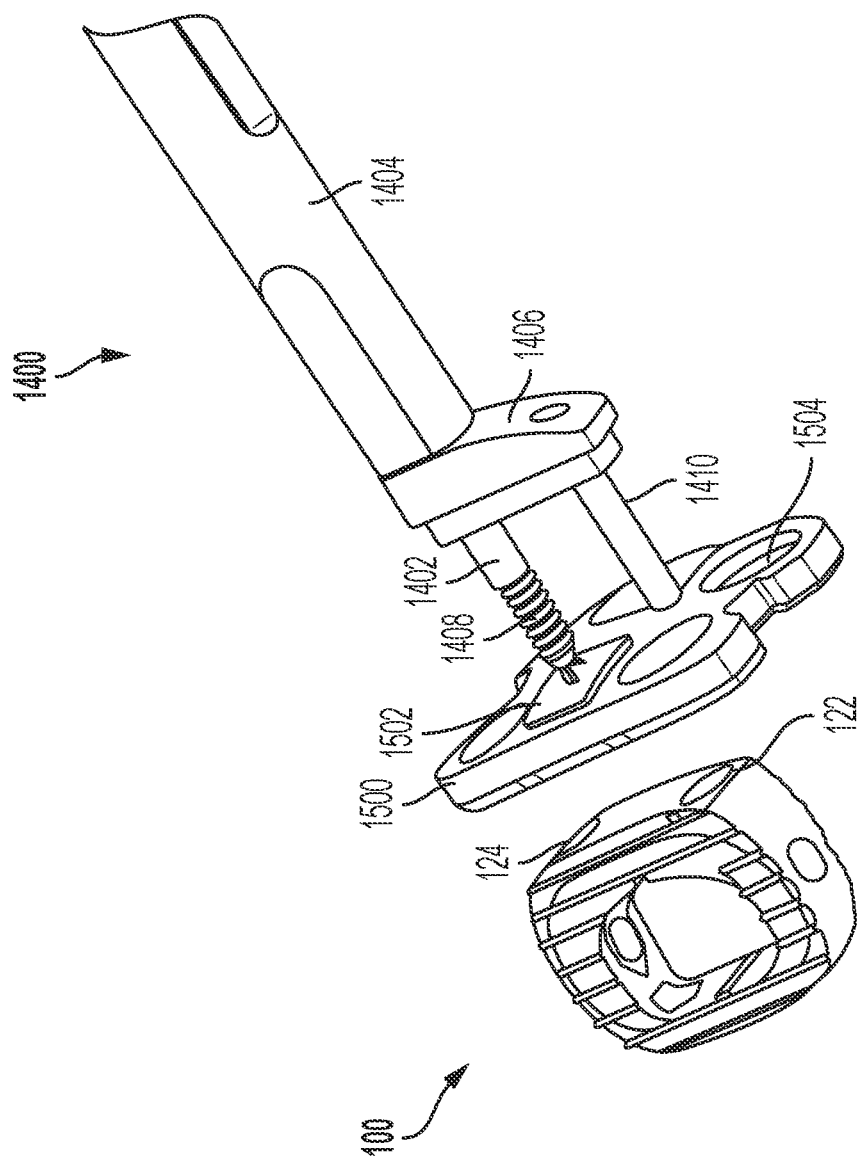
FIG. 43 is a schematic perspective view of the inserter of FIG. 42 engaging with the spinal implant of FIG. 1 and a spinal plate.

Referring now to FIG. 43, there is shown a method for placing spinal implant 100 by utilizing inserter 1400 according to another embodiment of the present invention. An anterior cervical plate 1500 can also simultaneously secured between inserter 1400 and spinal implant 100 prior to placement of the spinal implant as best shown in FIG. 43. Anterior cervical plate 1500 includes a plurality of screw holes 1504 for receiving bone screws and a plurality of blocker holes to receive blockers 1502. Blocker 1502 includes a washer and a retaining screw combination. Examples of bone plates that may be used with inserter 1400 are disclosed in U.S. Provisional Patent Application No. 62/653,877, the disclosure of which is hereby incorporated by reference herein. Threaded tip 1408 and alignment post 1410 are placed through the screw holes of anterior cervical plate 1500 and extend therethrough as best shown in FIG. 43. Inserter 1400 can now be engaged with spinal implant 100 by inserting alignment post 1410 into anti-rotation slot 122 and threadingly engaging threaded tip 1410 to threaded screw hole 124 by rotating knob 1412. After securing spinal implant 100 and anterior cervical plate 1500 to inserter 1400, an operator can precisely place this assembly to a target surgical site by utilizing the inserter 1400 to ensure precise alignment of spinal implant 100 and anterior cervical plate 1500 with reference to the surgical site. While spinal implant 100 and anterior cervical plate 1500 are shown in this embodiment, any other spinal implant and/or plate can be used in conjunction with the inserter disclosed herein. In other embodiments, the inserter can directly contact and place a spinal implant without a spinal plate.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A spinal implant comprising:
   an exterior solid frame defining medial, lateral, posterior and anterior edges, the posterior edge having a posterior thickness transverse to the posterior edge and the anterior edge having an anterior thickness transverse to the anterior edge, the anterior thickness being different from the posterior thickness, the exterior solid frame having one or more ribs extending between the medial and lateral edges, and
   a porous inner layer adjacent the exterior solid frame, the porous inner layer having superior and inferior surfaces,
   wherein the anterior thickness is defined by an extension of the anterior edge beyond the porous inner layer, and the posterior thickness is defined by an extension of the posterior edge beyond the porous inner layer.

2. The spinal implant of claim 1, wherein the ribs extend from the medial edge to the lateral edge.

3. The spinal implant of claim 1, wherein the posterior thickness is greater than the anterior thickness.

4. The spinal implant of claim 1, wherein the lateral edge has a lateral thickness transverse to the lateral edge and the medial edge has a medial thickness transverse to the medial edge, the lateral thickness and the medial thickness being at least 0.25 mm.

5. The spinal implant of claim 1, further including an upper surface and a lower surface, the upper and lower surfaces including the porous inner layer interspersed with the exterior solid frame.

6. The spinal implant of claim 1, further including an inner cavity extending in a superior-inferior direction and being defined by the porous inner layer and the exterior solid frame.

7. The spinal implant of claim 1, wherein the exterior solid frame is metal.

8. The spinal implant of claim 7, wherein the metal is titanium.

9. The spinal implant of claim 1, wherein the inner porous layer has a mean pore diameter between 400 and 500 microns.

10. The spinal implant of claim 1, wherein the implant is manufactured by an additive manufacturing process.

11. A spinal implant comprising:
an exterior frame defining medial, lateral, posterior and anterior walls, the posterior wall having a posterior wall thickness transverse to the posterior wall and the anterior wall having an anterior wall thickness transverse to the anterior wall, the anterior wall thickness being different from the posterior surface thickness, the exterior frame having one or more ribs extending between the medial wall and lateral wall,
an inner layer adjacent the solid frame, the inner layer having an exposed superior and an exposed inferior surface,
wherein the anterior wall thickness is defined by an extension of the anterior wall beyond the inner layer, and the posterior wall thickness is defined by an extension of the posterior wall beyond the inner layer, wherein the inner layer has a higher porosity than the exterior frame.

12. The spinal implant of claim 11, wherein the ribs extend from the medial wall to the lateral wall.

13. The spinal implant of claim 11, wherein the posterior wall thickness is greater than the anterior wall thickness.

14. The spinal implant of claim 11, wherein the lateral wall has a lateral wall thickness transverse to the lateral wall and the medial wall has a medial wall thickness transverse to the medial wall, the lateral wall thickness and the medial wall thickness being at least 0.25 mm.

15. The spinal implant of claim 11, further including an upper wall and a lower wall, the upper and lower walls including the inner layer interspersed with the exterior frame.

16. The spinal implant of claim 11, wherein the exterior frame is metal.

17. The spinal implant of claim 16, wherein the metal is titanium.

18. A spinal implant comprising:
an exterior solid frame defining medial, lateral, posterior and anterior walls, the posterior wall having a posterior wall thickness transverse to the posterior wall and the anterior wall having an anterior wall thickness transverse to the anterior wall, the anterior wall thickness being different from the posterior wall thickness;
a porous inner layer adjacent the exterior solid frame, and
upper and lower surfaces, each of the upper and lower surfaces comprising the porous inner layer interspersed between the exterior solid frame,
wherein the anterior wall thickness is defined by an extension of the anterior surface beyond the porous inner layer, and the posterior wall thickness is defined by an extension of the posterior surface beyond the porous inner layer.

19. The spinal implant of claim 18, wherein the posterior wall thickness is greater than the anterior wall thickness.

20. The spinal implant of claim 18, wherein the lateral wall has a lateral wall thickness transverse to the lateral wall and the medial wall has a medial wall thickness transverse to the medial wall, the lateral wall thickness and the medial wall thickness being at least 0.25 mm.

* * * * *